(12) United States Patent
Abdullah et al.

(10) Patent No.: US 8,791,330 B2
(45) Date of Patent: Jul. 29, 2014

(54) EXPRESSION REGULATORY ELEMENTS

(75) Inventors: Siti Nor Akmar Abdullah, Selangor (MY); Suan Choo Cheah, Putra Jaya (MY); Nurniwalis Abd. Wahab, Ampang (MY)

(73) Assignee: Malaysian Palm Oil Board, Selangor (MY)

( * ) Notice: Subject to any disclaimer, the term of this patent is extended or adjusted under 35 U.S.C. 154(b) by 1006 days.

(21) Appl. No.: 12/047,746

(22) Filed: Mar. 13, 2008

(65) Prior Publication Data

US 2008/0250532 A1    Oct. 9, 2008

(30) Foreign Application Priority Data

Mar. 13, 2007    (MY) .............................. PI 20070394

(51) Int. Cl.
*C12N 15/82*    (2006.01)
*C12N 15/63*    (2006.01)

(52) U.S. Cl.
USPC ........ 800/287; 536/24.1; 800/278; 435/320.1

(58) Field of Classification Search
USPC ....................................................... 800/287
See application file for complete search history.

(56) References Cited

U.S. PATENT DOCUMENTS

| | | | |
|---|---|---|---|
| 4,945,050 A | 7/1990 | Standford et al. | |
| 5,122,466 A | 6/1992 | Stomp et al. | |
| 6,235,971 B1 * | 5/2001 | Barry et al. | 800/278 |
| 7,375,209 B2 * | 5/2008 | Keetman et al. | 536/24.1 |
| 2010/0151109 A1 * | 6/2010 | Ragab et al. | 426/630 |

OTHER PUBLICATIONS

Kawakatsu et al. 2008, Journal of Experimental Botany 59:4233-4245.*
Beyer et al., Golden Rice: Introducing the β-Carotene Biosynthesis Pathway into rice endosperm by genetic engineering to defeat vitamin A deficiency, American Soc. for Nutr. Sci., 506S-510S (2002).
Bonaventure and Ohlrogge, "Differential Regulation of mRNA Levels of Acyl Carrier Protein Isoforms in *Arabidopsis*," Plant Physiol 128:223-235 (2002).
Daniell et al., "Medical molecular farming: production of antibodies, biopharmaceuticals and edible vaccines in plants," Trends in Plant Science 6(5):219-226 (2001).
Dickey et al., "Light Regulation of *Fed*-1 mRNA Requires an Element in the 5' Untranslated Region and Correlates with Differential Polyribosome Association," Plant Cell 10:475-484 (1998).
Kinney, "Development of genetically engineered soybean oils for food applications," J Food Lipids 10:273-292 (1996).
Müntz, "Deposition of storage proteins," Plant Mol. Biol. 38:77-99 (1998).
Ramli and Abdullah, "Development of a Transient Promoter Assay System for Palm Oil," J. Oil Palm Res. 15(2):62-69 (2003).
Tackaberry et al., "Increased yield of heterologous viral glycoprotein in the seeds of homozygous transgenic tobacco plants cultivated underground," Genome 46(3):521-526, 2003.
Takaiwa et al., "Sequence of three members and expression of a new major subfamily of glutelin genes from rice," Plant Mol. Biol. 17(4):875-885 (1991).
Voelker et al., "Fatty acid biosynthesis redirected to medium chains in transgenic oilseed plants," Science 257:72-74 (1992).

* cited by examiner

*Primary Examiner* — Li Zheng
(74) *Attorney, Agent, or Firm* — Fish & Richardson P.C.

(57) ABSTRACT

The present invention relates generally to an expression regulatory element operable in plants which includes oil palm, and in particular to an expression regulatory element operable selectively in the endosperm tissue of the plants. Said expression regulatory element comprises a sequence of nucleotides which specifically modulates the expression of a second nucleic acid molecule operably coupled to said expression regulatory element.

6 Claims, 16 Drawing Sheets

```
                                                    M  S  S  F  S
aagcaatagccttcagcgtttctctctttcttaatttctaaagccatgtcgtccttctct    60
L  L  S  F  S  L  C  L  L  L  L  C  R  V  S  Q  A  Q  F  G
ttgctctccttttctctttgcttgttgctcctgtgtcgtgtgtcccaggctcaatttggg   120
S  S  Q  E  S  P  F  Q  S  S  R  R  R  S  V  S  T  R  D  E
tccagtcaggagagcccatttcagagctcacgacgtcggtcggtatcaactcgggacgag   180
C  R  M  E  R  L  N  A  L  E  P  T  R  T  V  R  S  E  A  G
tgccggatggagaggctgaatgccctcgagccgacaaggactgtgaggtccgaagctggt   240
I  T  D  Y  F  D  E  D  N  E  Q  F  R  C  A  G  V  S  A  I
atcacggattactttgatgaggacaatgaacagttccggtgcgccggcgtgtccgcgatc   300
R  R  V  I  E  P  R  G  L  L  L  P  S  M  N  A  P  R  L
cgccgagtgatagaacccagaggccttctcctcccctccatgtccaatgcccctcgcctc   360
V  Y  I  V  Q  G  R  G  L  V  G  L  V  M  P  G  C  P  E  T
gtctacatcgtccaaggaaggggtctcgttggacttgtaatgcctggctgccccgaaact   420
F  Q  S  F  Q  R  S  E  Q  Y  E  R  E  E  G  E  R  H  R  R
ttccaatccttccagcgatccgagcagtatgaacgcgaggaaggcgagcgacatcggaga   480
S  R  D  E  H  Q  K  V  Y  Q  F  Q  E  G  D  V  L  A  V  P
tccagagatgaacaccaaaaagtctaccagttccaagagggagacgtcctggctgtgcct   540
D  G  F  A  Y  W  C  Y  N  N  G  E  N  P  V  V  A  I  T  V
gatggatttgcttactggtgctacaacaatggggagaaccctgtggtcgcgatcaccgtc   600
L  D  T  G  N  D  A  N  Q  L  D  R  S  H  R  Q  F  L  L  A
ctcgataccggtaacgatgctaaccagctcgatcgcagccacagacaattcttattggct   660
G  R  Q  E  E  G  R  Q  R  Y  R  R  G  E  S  I  K  E  N  I
ggaaggcaggaggaaggccggcaacgatatcgccgtggggagagcatcaaggaaaacatc   720
L  R  G  F  S  T  E  L  L  A  A  A  F  G  V  N  M  E  L  A
ctgagagggttcagcaccgagttgctggcagcggcttttggcgttaacatggagctggca   780
R  K  L  Q  C  R  D  D  T  R  G  E  N  V  R  A  E  N  G  L
aggaagctccagtgcagggatgacacaaggggcgagaacgtgcgggcggagaacgggctt   840
Q  V  L  R  P  S  R  M  E  E  E  R  E  E  S  R  R  K  N
caggtgctgaggcccctcaaggatggaggaagaagagagggaagagagtagaaggaaaat   900
G  L  E  E  T  Y  C  S  M  K  I  K  Q  N  I  G  D  P  R  R
ggattggaggagacctattgctcgatgaagattaagcagaacattggggatccaaggcgt   960
A  D  V  F  N  P  R  G  G  R  I  T  T  L  N  S  E  K  L  P
gccgacgtcttcaacccaaggggcggaaggattactaccctcaacagcgagaagcttccg  1020
I  L  R  F  I  Q  M  S  A  E  R  V  V  L  Y  R  N  A  M  V
atccttaggttcatccaaatgagtgctgagagggtggttctctacaggaacgccatggta  1080
S  P  H  W  N  I  N  A  H  S  I  M  Y  C  T  G  G  R  G  R
tcaccccactggaacatcaatgcccacagcatcatgtattgtaccggaggacgaggccgt  1140
V  E  V  A  D  D  K  G  E  T  A  F  D  G  E  L  R  Q  G  Q
gtcgaggttgctgatgacaagggagaaactgcgttcgacggagagctccgccaaggtcag  1200
L  L  I  V  P  Q  N  Y  A  V  S  E  R  A  G  S  E  G  F  Q
ctcttgatcgtcccgcaaaactatgcggtgtcggaaagggcgggaagtgaaggcttccag  1260
F  V  S  I  K  T  S  D  R  A  M  V  S  A  I  V  G  K  T  S
ttcgtatcgatcaagaccagcgaccgggccatggtgagcgcaatcgttgggaagacgtcg  1320
A  L  R  G  M  P  E  E  V  L  M  N  S  Y  R  I  S  R  D  E
gctctccggggcatgccggaggaggtgctgatgaactcctaccgcatctcaagggacgaa  1380
A  R  R  V  K  L  N  R  G  D  E  V  A  I  F  T  P  R  R  E
gcaaggagggtcaaactcaacaggggggacgaggtggcgatcttcactcctaggagagag  1440
S  R  A  E  A  *
tcgagagctgaagcttgatgcgatcttagcagggagtgctgctaggagtagagagacttt  1500
agtcatcagcggtggtggataagtaaatagagcctgaggttgctcttcgttctctgcata  1560
tgagaatataataataaaatgaaatgtccgcctgcgagcaagggcgaattccagcacact  1620
ggcggccgttactagtggatccgagctcggtaccaagcttgatgcatagcttgagtatt  1679
```

Nucleotide and deduced amino acid sequence of a full length oil palm cDNA clone (pOP-KT21) for a glutelin gene.

FIG. 1

| ALIGNMENT | 5'-UTR | 3'-UTR | CODING NUCLEOTIDES | | | AMINO ACIDS | | |
|---|---|---|---|---|---|---|---|---|
| | | | acidic subunit | basic subunit | overall | acidic subunit | basic subunit | overall |
| pOP-KT21 and pKT9 | 78.4 | 90.7 | 95.1 | 99.7 | 96.4 | 93.7 | 99.5 | 96 |
| pOP-KT21 and pKT7 | 43.6 | 48.1 | 66.7 | 74 | 69.8 | 49.7 | 70.4 | 57.4 |

PERCENTAGES OF IDENTITY (%)

Tabular representation summarizing percentages of identity at the nucleotide and amino acid levels between sequences of the different glutelin genes from oil palm.

FIG. 2

```
pOP-KT21      --MSSFSLLSFSLCLLLLCRVSQAQFGSSQE---SPFQSSRRRSVSTRDECRMERLNALE
pKT9          --MGSSSWLSFSLCLLLLCRMSQAQFGSSQE---SPFQSSRR-SVSTRNECRIERLNALE
pKT7          MVTSAATLLPFSLCLLLLCRPSLAQFE---R---SPRQSVRR--SGEQSQCGVEKHNALE
Glutelin-Rice MASINRPIVFFTVCLFLLCDGSLAQQLLGQST--SQWQSSRR---GSPRGCRFDRLQAFE
Globulin-sesame --MALTSLLSFFIVVTLLIRGLSAQLAGEQDFYWQDLQSQQQHKLQARTDCRVERLTAQE
                 . : * : :              . **  ::        * .::   * * pOP-KT21      PTRTVRSEAGITDYFDEDNEQFRCAGVSAIRRVIEPRGLLLPSMSNAPRLVYIVQGRGLV
pKT9          PTRTVRSEAGMTDYFDEDNEQFRCAGVSAIRRVIEPRGLLLPSMSNAPRLVYIVQGRGIV
pKT7          PIREVRSEAGVTEYY-QNNAQFECAGVAAFRRTIEPRGLLLPSFSNAPRLVYIIQGRGIY
Glutelin-Rice PIRSVRSQAGTTEFFDVSNELFQCTGVSVVRRVIEPRGLLLPHYTNGASLVYIIQGRGIT
Globulin-sesame PTIRFESEAGLTEFWDRNNQQFECAGVAAVRNVIQPRGLLLPHYNNAPQLLYVVRGRGIQ
               *   ..*:** *:::   .*   *.*:**:...*...*:******  .*.. *:*:::***:

pOP-KT21      GLVMPGCPETFQS-FQRSEQYEREE-GERHRRSRDEHQKVYQFQEGDVLAVPDGFAYWCY
pKT9          GLVMPGCPETFQS-FQRSERYEREE-GGRHRRPRDEHQKVYQFEEGDVLAVPNGFAYWCY
pKT7          GTVIPGCPETFQS-FQQSESEKQSE-KGQRQRFRDEHQRIHHFNQEDVIAIAAEVAHWCY
Glutelin-Rice GPTFPGCPETYQQQFQQSGQAQLTESQSQSHKFKDEHQKIHRFRQGDVIALPAGVAHWCY
Globulin-sesame GTVIPGCAETFER-----DTQPRQD---RRRRFMDRHQKVRQFRQGDILALPAGLTLWFY
               *  .:*.::    :          :  :: *.**::*:.: *::*:.  .: * * pOP-KT21      NNGENPVVAITVLDTGNDANQLDR--SHRQFLLAGRQEEGRQ------RYRRGESIKENI
pKT9          NNGENPVVAITVLDTSNDANQLDR--SHRQFLLAGRQEEGRQ------RYRREESMKENI
pKT7          TDADTPVIAFTVSDISTARISLMKTIGNSYWLGDGVAAGGNL------GKNKNRAQRATS
Glutelin-Rice NDGEVPVVAIYVTDINNGANQLDP--RQRDFLLAGNKRNPQA------YRREVEEWSQNI
Globulin-sesame NNGGEPLITVALLDTGNAANQLDQ--TFRHFFLAGNPQGGRQSYFGRPQTEKQQGETKNI
               .:.  *:::.  : * ..   .*      ::   *             .   ..  .

pOP-KT21      LRGFSTELLAAAFGVNMELARKLQCRDDTRGENVRAENGLQVLRPSRMEEEERE---ESR
pKT9          LRGFSTELLAAAFGVNMELARKLQCRDDTRGEMVRAENGLQVLRPSRMEEEERE---ESR
pKT7          LADSIPSYWRPAIGVDREVARKLQCKDDQRGEIVRVEKGLEVLRPSSEKQEREE---RGR
Glutelin-Rice FSGFSTELLSEAFGISNQVARQLQCQNDQRGEIVRVERGLSLLQPYASLQEQEQGQMQSR
Globulin-sesame FNGFDDEILADAFGVDVQTARRLKGQDDLRGRIVRAER-LDIVLPGEEEEERWERDPYSG
               :  .     *:*:.  : **:*:  ::* **..**.*. *.:: *     :*. :

pOP-KT21      ----------------RKNGLEETYCSMKIKQNIGDPRRADVFNPRGGRITTLNSEKLPI
pKT9          ----------------RKNGLEETYCSMKIKQNIGDPRRADVFNPRGGRITTLNSEKLPI
pKT7          ----------------GTNGLEVAMCSMRNRENIDSSRRADVYIPRGGRITNLNSQKLPM
Glutelin-Rice EHYQEGGYQQSQYGSGCPNGLDETFCTMRVRQNIDNPNRADTYNPRAGRVTNLNSQNFPI
Globulin-sesame ----------------ANGLEETLCTAKLRENLDEPARADVYNPHGGRISSLNSLTLPV
                                ***:   : *:  : ::*:....***.:  *::::.*  ..:* pOP-KT21      LRFIQMSAERVVLYRNAMVSPHWNINAHSIMYCTGGRGRVEVADDKGETAFDGELRQGQL
pKT9          LRFIQMSAERVVLYRNAMVSPHWNINAHSIMYCTGGRGGVEVADDKGETAFDGELRQGQL
pKT7          LSFIQLSAERVVLYKNAMLAPHWNINAHSVTYCTGGRGGVQVVDNNGKTVFDGELRQGQL
Glutelin-Rice LNLVQMSAVKVNLYQNALLSPFWNINAHSIVYITQGRAQVQVVNNNGKTVFNGELRRGQL
Globulin-sesame LSWLRLSAEKGVLYRNGLVAPHWNLNAHSIIYITRGSGRFQVVGHTGRSVFDGVVREGQL
               *  :::   :   :  **:.::::*.:**;  *   *  . .:*....*:*  :* :*.*** pOP-KT21      LIVPQNYAVSERAGS-EGFQFVSIKTSDRAMVSAIVGKTSALRGMPEEVLMNSYRISRDE
pKT9          LIVPQNYAVSERAGS-EGFQFVSIKTSDRAMVSAIVGKTSALRGMPEEVLMNSYRISRDE
pKT7          LVIPQNFAVIKQAGN-EGFEFTSIKTIDNAMVNTIVGKASAFQGMPEEVLMNSYRINRNE
Glutelin-Rice LIVPQHYVVVKKAQR-EGCAYIAFKTNPNSMVSHIAGKSSIFRALPTDVLANAYRISREE
Globulin-sesame IIVPQNYVVAKRASQDEGLEWISFKTNDNAMTSQLAGRLSAIRAMPEEVVMTAYQVSRDE
               :::**::.* ::*       : :: ..:*.. :.*: *   :::* *: ..:*::.*:* pOP-KT21      ARRVKLNRGDEVAIFT-------PRR--------ESRAEA--------
pKT9          ARRVKLNRGDEVAIFT-------PRR--------ESRAEA--------
pKT7          ARTVKFNRGHEMAIFS-------PRS--------EGRADA--------
Glutelin-Rice AQRLKHNRGDEFGAFT-------PLQY-------KSYQDVYNVAESS-
Globulin-sesame ARRLKYNR-EESRVFSSTSRYSWPRSSRPMSYMPKPFEYVLDVIKSMM
               *: :* ** .*   *:       *             :      .
```

Comparison between the deduced amino acid sequences of oil palm glutelin genes with that of the rice glutelin gene (P07730) and sesame 11S globulin gene (AF240004).

FIG. 3

AMINO USAGE
Total_Amino(The number of amino acid) = 470
Molecular Weight = 53580.71

| Amino Acid | Count | Mol (Percent) |
|---|---|---|
| Ala(A) | 31 | 6.60 |
| Arg(R) | 59 | 12.55 |
| Asn(N) | 22 | 4.68 |
| Asp(D) | 20 | 4.26 |
| Cys(C) | 9 | 1.91 |
| Gln(Q) | 24 | 5.11 |
| Glu(E) | 46 | 9.79 |
| Gly(G) | 35 | 7.45 |
| His(H) | 5 | 1.06 |
| Ile(I) | 19 | 4.04 |
| Leu(L) | 38 | 8.09 |
| Lys(K) | 11 | 2.34 |
| Met(M) | 13 | 2.77 |
| Phe(F) | 19 | 4.04 |
| Pro(P) | 17 | 3.62 |
| Ser(S) | 39 | 8.30 |
| Thr(T) | 17 | 3.62 |
| Trp(W) | 2 | 0.43 |
| Tyr(Y) | 12 | 2.55 |
| Val(V) | 32 | 6.81 |
| Total | 470 | 99.99 |

A tabular representation showing a comparison between the amino acid profiles of the deduced amino acid sequence of pOP-KT21 (A) and the amino acid composition of palm kernel meal (B).

FIG. 4A

| Amino acids | Composition of Amino Acid in Palm Kernel meal (g/kg) |
|---|---|
| Arginine | 23.6 |
| Cystine | 2.8 |
| Glycine | 8.1 |
| Histidine | 3.2 |
| Leucine | 11.9 |
| Isoleucine | 6.4 |
| Lysine | 5.4 |
| Methionine | 3.3 |
| Phenylalanine | 7.9 |
| Threonine | 6.1 |
| Tryptophan | 2.0 |
| Tyrosine | 4.7 |
| Valine | 8.2 |

AMINO ACID COMPOSITION OF PALM KERNEL MEAL
(g/kg) (Fresh Basis) (Siew, 1989)

FIG. 4B

Expression pattern of the oil palm glutelin gene (subfamily B) in different oil palm tissues determined by slot blot analysis using labeled pOP-KT21 EST as probe.

Expression pattern of the oil palm glutelin gene (subfamily B) in different oil palm tissues determined by northern blot analysis using labeled probe containing pOP-KT21 cDNA sequence.

Expression pattern of pOP-KT21 in different oil palm tissues determined by northern blot analysis using labeled gene-specific probe from 5'-UTR and 5'-end coding region of pOP-KT21.

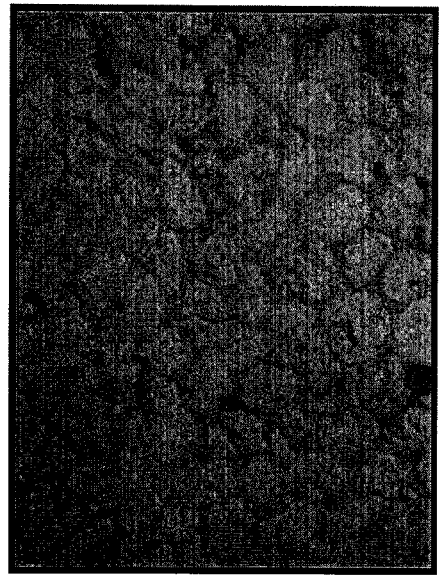
Panel (a)
Sense RNA Probe
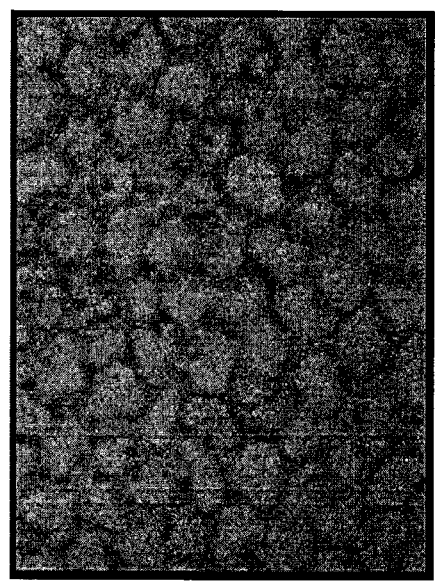
Panel (b)
Antisense RNA Probe
Cell-specific expression pattern of oil palm glutelin gene (subfamily B) in the endosperm tissue of the oil palm determined by RNA *in situ* hybridization using sense (panel a) and antisense (panel b) RNA probe prepared using oil palm pOP-KT21 EST.
FIG. 8

Product of genome walking reaction for isolating pOP-KT21 gene promoter

```
TCAAATTATC AAAATATCTC CAATAATTTT ATCCTGATGC TTTTCTTTTT   -1296
TTTTTAGTAA GAAGTGGTGG AAGTGGTATG GGTGTAGTGG TGACACGAAG   -1246
AAGCGGTGGC TGGAGGGTGT AAAAAATTGT GGGCATGGGG GGAGAGGGTG   -1196
GGTGTGCGCG GAGGAGCTAA GGGGGTGGTG GAGACGAGCG TGGAGGAGCC   -1146
GCAGGGGGGA GAGTGGTGGG GGTGGAGGGT AGAGGAGCCA TGGACAAGCG   -1096
AGGGGGTGGA GGAGCCACAA GTCGTGGGGG AGCAGTGTGC TTAAAGGAGC   -1046
TAGTGGGTGG TGGGATGAG CATGGAAGAG CTGCGGGGGA TGGTGGGGGA    -996
           Skn-1-like motif
TGAGGGAGGA GGAGTCATGG GCAGGCAAGG GGGTGGAGAA GTCACAGGTC    -946
AGGAGGGTGA TAAAGGAGCC ATGGGTAGGT GGTGGGGCAG AGGAGCTGCG    -896
GGCAAGCGGT AGAGATGGAC GAGCCATAGG TGATGCCGGG GGAGGGGTCG    -846
GGAAGGAGGG GGAGCGTTGG GCTATGGGTT TTATGTTTTT CTTTTTAAGG    -796
GATAATTTTA TCCAAAATTT TTATTGCAAT ACTGTCAAAA AAGTGGTAAT    -746
CTGATTAGCC ATTTCTTTCC GAGGCTATTT AAATTATCTC ATAGGAGGTA    -696
ATATAGATTG TCAAGACAAT TTGGATTGCC ACCCAAAAGC ATCCCAAATG    -646
CAGTAATCCA ATGGAGCCAC TTTAAATTGC TGACGATCTA AATAGATTAC    -596
CAGCTACCAA ATGCAACATA AAGCTAACT CCCAAGCTTG CATTGCTTGC     -546
TAAATCTGTA GCACGTAGTC CTTGGACTCT TGATTTGTT TGTCTTTTGA     -496
AAAATTTCTT TGGACTTCAG TATACTTCTC ATCTATCATA TTATACCTTA    -446
GGTCACTTAG CATTTTTAGA AGAAAGAGAT GTTATTTTGA AAATAAAAAA    -396
CTCTAACAGC ATACTAATTG AACAAGATCA TCAGAATACT TGGCAGGACC    -346
AAGAGGGATA GGAGCTAGCC CACCCAGCAA TATATATAAT TCACTGAAAT    -296
CATCTGATCT ACTCTTGCAT TCTGATGTGC TTGCTGCAAG CGGTTGGTAC    -246
GGTTGTCCTC TTCCTTCCAA TATTTACAGT CCATTCATCC AAGTGTATGA    -196
CACGTGGCCA CCTGTATTCT GTCCTCTCTG GACCAAGCTG CCACGCACCC    -146
ATCTCCATAT ATCTTATGCG GCAACACGAG AGCTCATGCA TGGCAAAGCA     -96
                                                      AACA motif
TGGGCGTCGT ATCTCACAAA AGTGCATCCA GATGGGTCCA AGCCTAAACA     -46
           TATA box                      Transcription start
ACTTTTTTGG CCTATAAATG CCCACCCCAT CTCGCCACCC TTGCTCAAGC      4
AATA                                                       8
```

The sequence of the oil palm glutelin gene (pOP-KT21) promoter.

FIG. 10

```
              1 . . . . . . . . . 10 . . . . . . . . .20  . . . . . . . . .30
    KT21-Pa   A A G C A A T A G C  C T T C A G C G T T   T C T C T C T T T C
    KT21-cDNA A A G C A A T A G C  C T T C A G C G T T   T C T C T C T T T C

Consensus A A G C A A T A G C  C T T C A G C G T T   T C T C T C T T T C

. . . . . . . . . .40  . . . . . . . . .50  . . . . . . . . .60
    KT21-Pa   T T A A T T T C T A   A A G C C A T G T C   G T C C T T C T C T
    KT21-cDNA T T A A T T T C T A   A A G C C A T G T C   G T C C T T C T C T

Consensus T T A A T T T C T A   A A G C C A T G T C   G T C C T T C T C T

. . . . . . . . . .70  . . . . . . . . .80  . . . . . . . . .90
    KT21-Pa   T T G C T C T C C T   T T T C T C T T T G   C T T G T T G C T C
    KT21-cDNA T T G C T C T C C T   T T T C T C T T T G   C T T G T T G C T C

Consensus T T G C T C T C C T   T T T C T C T T T G   C T T G T T G C T C

. . . . . . . . .100  . . . . . . . . .110  . . . . . . . .120
    KT21-Pa   C T G T G T C G T G   T G T C C C A G G C   T C A A T T T G G G
    KT21-cDNA C T G T G T C G T G   T G T C C C A G G C   T C A A T T T G G G

Consensus C T G T G T C G T G   T G T C C C A G G C   T C A A T T T G G G

. . . . . . . . .130  . . . . . . . . .140  . . . . . . . .150
    KT21-Pa   T C C A G T C A
    KT21-cDNA T C C A G T C A

Consensus T C C A G T C A
```

DNA sequence alignment of pKT21-Pa (genomic sequence)
and pOP-KT21 (cDNA sequence)

FIG. 11

Restriction analysis of the chimeric transformation vector GluP-EGFP.

| Tissue slices | Distance between macrocarrier and target tissues | Helium pressure | No. of fluorescent spots |
|---|---|---|---|
| Outer layer of endosperm | 9 cm | 1550 Psi | Plate 1 – 88<br>Plate 2 - 230 |
| Inner layer of endosperm | 9 cm | 1550 Psi | Plate 1 – 6<br>Plate 2 - 7 |
| Inner layer of endosperm | 9 cm | 1350 Psi | Plate 1 – 1<br>Plate 2 - 2 |
| Inner layer of endosperm | 9 cm | 1880 Psi | Plate 1 – 3<br>Plate 2 - 6 |

Tabular representation showing optimized bombardment parameters for transient assay analysis using oil palm kernel tissue slices

FIG. 13

Promoter-reporter gene assay to confirm endosperm-specific activity of the oil palm glutelin gene promoter (GluP) by comparing expression of green fluorescent protein in oil palm endosperm, mesocarp and leaf tissues bombarded with GluP-EGFP and CaMV-EGFP.

| Tissues \ Vector | GluP-EGFP | CaMV-EGFP | pEGFP |
|---|---|---|---|
| endosperm | 7 ± 1 | 45 ± 2.5 | 0 |
| mesocarp | 0 | 71 ± 1.4 | 0 |
| leaves | 0 | 170 ± 9.1 | 0 |

Tabular representation showing counts of GFP spots in leaf, mesocarp and kernel tissues bombarded with GluP-EGFP, CaMV-EGFP and pEGFP

FIG. 15

SEQUENCE LISTING

<160> NUMBER OF SEQ ID NOS: 19

<210> SEQ ID NO 1
<211> LENGTH: 1679
<212> TYPE: DNA
<213> ORGANISM: Elaeis guineensis

<400> SEQUENCE: 1
aagcaatagc cttcagcgtt tctctctttc ttaatttcta aagccatgtc gtccttctct        60

```
ttgctctcct tttctctttg cttgttgctc ctgtgtcgtg tgtcccaggc tcaatttggg      120
tccagtcagg agagcccatt tcagagctca cgacgtcggt cggtatcaac tcgggacgag      180
tgccggatgg agaggctgaa tgccctcgag ccgacaagga ctgtgaggtc cgaagctggt      240
atcacggatt actttgatga ggacaatgaa cagttccggt cgccggcgt gtccgcgatc       300
cgccgagtga tagaacccag aggccttctc ctcccctcca tgtccaatgc ccctcgcctc      360
gtctacatcg tccaaggaag gggtctcgtt ggacttgtaa tgcctggctg ccccgaaact      420
ttccaatcct tccagcgatc cgagcagtat gaacgcgagg aaggcgagcg acatcggaga      480
tccagagatg aacaccaaaa agtctaccag ttccaagagg gagacgtcct ggctgtgcct      540
gatggatttg cttactggtg ctacaacaat ggggagaacc ctgtggtcgc gatcaccgtc      600
ctcgataccg gtaacgatgc taaccagctc gatcgcagcc acagacaatt cttattggct      660
ggaaggcagg aggaaggccg gcaacgatat cgccgtgggg agagcatcaa ggaaaacatc      720
ctgagagggt tcagcaccga gttgctggca gcggcttttg gcgttaacat ggagctggca      780
aggaagctcc agtgcaggga tgacacaagg ggcgagaacg tgcgggcgga gaacgggctt      840
caggtgctga ggccctcaag gatggaggaa gaagagaggg aagagagtag aaggaaaaat      900
ggattggagg agacctattg ctcgatgaag attaagcaga acattgggga tccaaggcgt      960
gccgacgtct caacccaag gggcggaagg attactaccc tcaacagcga gaagcttccg       1020
atccttaggt tcatccaaat gagtgctgag agggtggttc tctacaggaa cgccatggta      1080
tcacccact ggaacatcaa tgcccacagc atcatgtatt gtaccggagg acgaggccgt       1140
gtcgaggttg ctgatgacaa gggagaaact gcgttcgacg gagagctccg ccaaggtcag      1200
ctcttgatcg tcccgcaaaa ctatgcggtg tcggaaaggg cgggaagtga aggcttccag      1260
ttcgtatcga tcaagaccag cgaccgggcc atggtgagcg caatcgttgg gaagacgtcg      1320
gctctccggg gcatgccgga ggaggtgctg atgaactcct accgcatctc aagggacgaa      1380
gcaaggaggg tcaaactcaa caggggggac gaggtggcga tcttcactcc taggagagag      1440
tcgagagctg aagcttgatg cgatcttagc agggagtgct gctaggagta gagagacttt      1500
agtcatcagc ggtggtggat aagtaaatag agcctgaggt tgctcttcgt tctctgcata      1560
tgagaatata ataataaaat gaaatgtccg cctgcgagca agggcgaatt ccagcacact      1620
ggcggccgtt actagtggat ccgagctcgg taccaagctt gatgcatagc ttgagtatt      1679
```

<210> SEQ ID NO 2
<211> LENGTH: 470
<212> TYPE: PRT
<213> ORGANISM: Elaeis guineensis

<400> SEQUENCE: 2

Met Ser Ser Phe Ser Leu Leu Ser Phe Ser Leu Cys Leu Leu Leu Leu
 1               5                  10                  15

Cys Arg Val Ser Gln Ala Gln Phe Gly Ser Ser Gln Glu Ser Pro Phe
            20                  25                  30

Gln Ser Ser Arg Arg Arg Ser Val Ser Thr Arg Asp Glu Cys Arg Met
        35                  40                  45

Glu Arg Leu Asn Ala Leu Glu Pro Thr Arg Thr Val Arg Ser Glu Ala
    50                  55                  60

Gly Ile Thr Asp Tyr Phe Asp Glu Asp Asn Glu Gln Phe Arg Cys Ala
65                  70                  75                  80

Gly Val Ser Ala Ile Arg Arg Val Ile Glu Pro Arg Gly Leu Leu Leu

```
                        85                  90                  95
        Pro Ser Met Ser Asn Ala Pro Arg Leu Val Tyr Ile Val Gln Gly Arg
                        100                 105                 110

Gly Leu Val Gly Leu Val Met Pro Gly Cys Pro Glu Thr Phe Gln Ser
                        115                 120                 125

Phe Gln Arg Ser Glu Gln Tyr Glu Arg Glu Gly Glu Arg His Arg
                130                 135                 140

Arg Ser Arg Asp Glu His Gln Lys Val Tyr Gln Phe Gln Glu Gly Asp
        145                 150                 155                 160

Val Leu Ala Val Pro Asp Gly Phe Ala Tyr Trp Cys Tyr Asn Asn Gly
                            165                 170                 175

Glu Asn Pro Val Val Ala Ile Thr Val Leu Asp Thr Gly Asn Asp Ala
                        180                 185                 190

Asn Gln Leu Asp Arg Ser His Arg Gln Phe Leu Leu Ala Gly Arg Gln
                        195                 200                 205

Glu Glu Gly Arg Gln Arg Tyr Arg Arg Gly Glu Ser Ile Lys Glu Asn
                        210                 215                 220

Ile Leu Arg Gly Phe Ser Thr Glu Leu Leu Ala Ala Ala Phe Gly Val
        225                 230                 235                 240

Asn Met Glu Leu Ala Arg Lys Leu Gln Cys Arg Asp Asp Thr Arg Gly
                            245                 250                 255

Glu Asn Val Arg Ala Glu Asn Gly Leu Gln Val Leu Arg Pro Ser Arg
                        260                 265                 270

Met Glu Glu Glu Arg Glu Glu Ser Arg Arg Lys Asn Gly Leu Glu
                275                 280                 285

Glu Thr Tyr Cys Ser Met Lys Ile Lys Gln Asn Ile Gly Asp Pro Arg
                        290                 295                 300

Arg Ala Asp Val Phe Asn Pro Arg Gly Arg Ile Thr Thr Leu Asn
        305                 310                 315                 320

Ser Glu Lys Leu Pro Ile Leu Arg Phe Ile Gln Met Ser Ala Glu Arg
                        325                 330                 335

Val Val Leu Tyr Arg Asn Ala Met Val Ser Pro His Trp Asn Ile Asn
                        340                 345                 350

Ala His Ser Ile Met Tyr Cys Thr Gly Gly Arg Gly Arg Val Glu Val
                        355                 360                 365

Ala Asp Asp Lys Gly Glu Thr Ala Phe Asp Gly Glu Leu Arg Gln Gly
                        370                 375                 380

Gln Leu Leu Ile Val Pro Gln Asn Tyr Ala Val Ser Glu Arg Ala Gly
        385                 390                 395                 400

Ser Glu Gly Phe Gln Phe Val Ser Ile Lys Thr Ser Asp Arg Ala Met
                            405                 410                 415

Val Ser Ala Ile Val Gly Lys Thr Ser Ala Leu Arg Gly Met Pro Glu
                        420                 425                 430

Glu Val Leu Met Asn Ser Tyr Arg Ile Ser Arg Asp Glu Ala Arg Arg
                        435                 440                 445

Val Lys Leu Asn Arg Gly Asp Glu Val Ala Ile Phe Thr Pro Arg Arg
        450                 455                 460

Glu Ser Arg Ala Glu Ala
        465                 470

<210> SEQ ID NO 3
<211> LENGTH: 1354
<212> TYPE: DNA
<213> ORGANISM: Elaeis guineensis
```

<400> SEQUENCE: 3

```
tcaaattatc aaaatatctc caataatttt atcctgatgc ttttcttttt tttttagtaa      60
gaagtggtgg aagtggtatg ggtgtagtgg tgacacgaag aagcggtggc tggagggtgt     120
aaaaaattgt gggcatgggg ggagagggtg ggtgtgcgcg gaggagctaa gggggtggtg     180
gagacgagcg tggaggagcc gcagggggga gagtggtggg ggtggagggt agaggagcca     240
tggacaagcg aggggtgga ggagccacaa gtcgtgggg agcagtgtgc ttaaaggagc       300
tagtgggtgg tggggatgag catggaagag ctgcggggga tggtggggga tgaggagga     360
ggagtcatgg gcaggcaagg gggtggagaa gtcacaggtc aggagggtga taaaggagcc     420
atgggtaggt ggtggggcag aggagctgcg ggcaagcggt agagatggac gagccatagg     480
tgatgccggg ggaggggtcg ggaaggaggg ggagcgttgg gctatgggtt ttatgttttt     540
cttttttaagg gataattttta tccaaaattt ttattgcaat actgtcaaaa aagtggtaat     600
ctgattagcc atttctttcc gaggctattt aaattatctc ataggaggta atatagattg     660
tcaagacaat ttggattgcc acccaaaagc atcccaaatg cagtaatcca atggagccac     720
tttaaattgc tgacgatcta aatagattac cagctaccaa atgcaacata aaggctaact     780
cccaagcttg cattgcttgc taaatctgta gcacgtagtc cttggactct tgattttgtt     840
tgtcttttga aaaatttctt tggacttcag tatacttctc atctatcata ttataccttta    900
ggtcacttag cattttttaga agaaagagat gttattttga aaataaaaaa ctctaacagc    960
atactaattg aacaagatca tcagaatact tggcaggacc aagagggata ggagctagcc   1020
cacccagcaa tatatataat tcactgaaat catctgatct actcttgcat tctgatgtgc   1080
ttgctgcaag cggttggtac ggttgtcctc ttccttccaa tatttacagt ccattcatcc   1140
aagtgtatga cacgtggcca cctgtattct gtcctctctg gaccaagctg ccacgcaccc   1200
atctccatat atcttatgcg gcaacacgag agctcatgca tggcaaagca tgggcgtcgt   1260
atctcacaaa agtgcatcca gatgggtcca agcctaaaca acttttttgg cctataaatg   1320
cccacccat ctcgccaccc ttgctcaagc aata                                 1354
```

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4

```
cctgccttcc agccaataag                                                  20
```

<210> SEQ ID NO 5
<211> LENGTH: 16
<212> TYPE: DNA
<213> ORGANISM: Artificial Sequence
<220> FEATURE:
<223> OTHER INFORMATION: Primer

<400> SEQUENCE: 5

```
cttcccccc ccccc                                                        16
```

<210> SEQ ID NO 6
<211> LENGTH: 19
<212> TYPE: DNA
<213> ORGANISM: Artificial Sequence
<220> FEATURE:

<223> OTHER INFORMATION: Primer

<400> SEQUENCE: 6
gatcgcgacc acagggttc                                              19

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
caatagcctt cagcgtttc                                              19

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gagaaggacg acatggct                                               18

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
gactggaccc aaattgagcc tgggacac                                    28

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
gaaagagaga aacgctgaag gctattgc                                    28

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
ccgctcgagt caaattatca aaatatc                                     27

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cgcggatcca agagagaaac gctg                                        24

-continued

```
<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
aagcaatagc cttcagcgtt tc                                              22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gcccttgctc gcaggcggag                                                 20

<210> SEQ ID NO 15
<211> LENGTH: 469
<212> TYPE: PRT
<213> ORGANISM: Elaeis guineensis

<400> SEQUENCE: 15

Met Gly Ser Ser Trp Leu Ser Phe Ser Leu Cys Leu Leu Leu
 1               5                  10                  15

Cys Arg Met Ser Gln Ala Gln Phe Gly Ser Ser Gln Glu Ser Pro Phe
            20                  25                  30

Gln Ser Ser Arg Arg Ser Val Ser Thr Arg Asn Glu Cys Arg Ile Glu
        35                  40                  45

Arg Leu Asn Ala Leu Glu Pro Thr Arg Thr Val Arg Ser Glu Ala Gly
    50                  55                  60

Met Thr Asp Tyr Phe Asp Glu Asp Asn Glu Gln Phe Arg Cys Ala Gly
65                  70                  75                  80

Val Ser Ala Ile Arg Arg Val Ile Glu Pro Arg Gly Leu Leu Leu Pro
                85                  90                  95

Ser Met Ser Asn Ala Pro Arg Leu Val Tyr Ile Val Gln Gly Arg Gly
            100                 105                 110

Ile Val Gly Leu Val Met Pro Gly Cys Pro Glu Thr Phe Gln Ser Phe
        115                 120                 125

Gln Arg Ser Glu Arg Tyr Glu Arg Glu Gly Gly Arg His Arg Arg
    130                 135                 140

Pro Arg Asp Glu His Gln Lys Val Tyr Gln Phe Glu Glu Gly Asp Val
145                 150                 155                 160

Leu Ala Val Pro Asn Gly Phe Ala Tyr Trp Cys Tyr Asn Asn Gly Glu
                165                 170                 175

Asn Pro Val Val Ala Ile Thr Val Leu Asp Thr Ser Asn Asp Ala Asn
            180                 185                 190

Gln Leu Asp Arg Ser His Arg Gln Phe Leu Leu Ala Gly Arg Gln Glu
        195                 200                 205

Glu Gly Arg Gln Arg Tyr Arg Arg Glu Glu Ser Met Lys Glu Asn Ile
    210                 215                 220

Leu Arg Gly Phe Ser Thr Glu Leu Leu Ala Ala Phe Gly Val Asn
225                 230                 235                 240

Met Glu Leu Ala Arg Lys Leu Gln Cys Arg Asp Asp Thr Arg Gly Glu
                245                 250                 255
```

```
Met Val Arg Ala Glu Asn Gly Leu Gln Val Leu Arg Pro Ser Arg Met
                260                 265                 270

Glu Glu Glu Glu Arg Glu Ser Arg Arg Lys Asn Gly Leu Glu Glu
        275                 280                 285

Thr Tyr Cys Ser Met Lys Ile Lys Gln Asn Ile Gly Asp Pro Arg Arg
    290                 295                 300

Ala Asp Val Phe Asn Pro Arg Gly Gly Arg Ile Thr Thr Leu Asn Ser
305                 310                 315                 320

Glu Lys Leu Pro Ile Leu Arg Phe Ile Gln Met Ser Ala Glu Arg Val
                325                 330                 335

Val Leu Tyr Arg Asn Ala Met Val Ser Pro His Trp Asn Ile Asn Ala
            340                 345                 350

His Ser Ile Met Tyr Cys Thr Gly Gly Arg Gly Gly Val Glu Val Ala
                355                 360                 365

Asp Asp Lys Gly Glu Thr Ala Phe Asp Gly Glu Leu Arg Gln Gly Gln
370                 375                 380

Leu Leu Ile Val Pro Gln Asn Tyr Ala Val Ser Glu Arg Ala Gly Ser
385                 390                 395                 400

Glu Gly Phe Gln Phe Val Ser Ile Lys Thr Ser Asp Arg Ala Met Val
                405                 410                 415

Ser Ala Ile Val Gly Lys Thr Ser Ala Leu Arg Gly Met Pro Glu Glu
                420                 425                 430

Val Leu Met Asn Ser Tyr Arg Ile Ser Arg Asp Glu Ala Arg Arg Val
                435                 440                 445

Lys Leu Asn Arg Gly Asp Glu Val Ala Ile Phe Thr Pro Arg Arg Glu
                450                 455                 460

Ser Arg Ala Glu Ala
465
```

<210> SEQ ID NO 16
<211> LENGTH: 468
<212> TYPE: PRT
<213> ORGANISM: Elaeis guineensis

<400> SEQUENCE: 16

```
Met Val Thr Ser Ala Ala Thr Leu Leu Pro Phe Ser Leu Cys Leu Leu
1               5                   10                  15

Leu Leu Cys Arg Pro Ser Leu Ala Gln Phe Glu Arg Ser Pro Arg Gln
                20                  25                  30

Ser Val Arg Arg Ser Gly Glu Gln Ser Gln Cys Gly Val Glu Lys His
            35                  40                  45

Asn Ala Leu Glu Pro Ile Arg Glu Val Arg Ser Glu Ala Gly Val Thr
50                  55                  60

Glu Tyr Tyr Gln Asn Asn Ala Gln Phe Glu Cys Ala Gly Val Ala Ala
65                  70                  75                  80

Phe Arg Arg Thr Ile Glu Pro Arg Gly Leu Leu Leu Pro Ser Phe Ser
                85                  90                  95

Asn Ala Pro Arg Leu Val Tyr Ile Ile Gln Gly Arg Gly Ile Tyr Gly
                100                 105                 110

Thr Val Ile Pro Gly Cys Pro Glu Thr Phe Gln Ser Phe Gln Gln Ser
                115                 120                 125

Glu Ser Glu Lys Gln Ser Glu Lys Gly Gln Arg Gln Arg Phe Arg Asp
    130                 135                 140

Glu His Gln Arg Ile His His Phe Asn Gln Glu Asp Val Ile Ala Ile
145                 150                 155                 160
```

```
Ala Ala Glu Val Ala His Trp Cys Tyr Thr Asp Ala Asp Thr Pro Val
            165                 170                 175

Ile Ala Phe Thr Val Ser Asp Ile Ser Thr Ala Arg Ile Ser Leu Met
            180                 185                 190

Lys Thr Ile Gly Asn Ser Tyr Trp Leu Gly Asp Gly Val Ala Ala Gly
            195                 200                 205

Gly Asn Leu Gly Lys Asn Lys Asn Arg Ala Gln Arg Ala Thr Ser Leu
            210                 215                 220

Ala Asp Ser Ile Pro Ser Tyr Trp Arg Pro Ala Ile Gly Val Asp Arg
225                 230                 235                 240

Glu Val Ala Arg Lys Leu Gln Cys Lys Asp Asp Gln Arg Gly Glu Ile
            245                 250                 255

Val Arg Val Glu Lys Gly Leu Glu Val Leu Arg Pro Ser Ser Glu Lys
            260                 265                 270

Gln Glu Arg Glu Glu Arg Gly Arg Gly Thr Asn Gly Leu Glu Val Ala
            275                 280                 285

Met Cys Ser Met Arg Asn Arg Glu Asn Ile Asp Ser Ser Arg Arg Ala
            290                 295                 300

Asp Val Tyr Ile Pro Arg Gly Gly Arg Ile Thr Asn Leu Asn Ser Gln
305                 310                 315                 320

Lys Leu Pro Met Leu Ser Phe Ile Gln Leu Ser Ala Glu Arg Val Val
            325                 330                 335

Leu Tyr Lys Asn Ala Met Leu Ala Pro His Trp Asn Ile Asn Ala His
            340                 345                 350

Ser Val Thr Tyr Cys Thr Gly Gly Arg Gly Gly Val Gln Val Val Asp
            355                 360                 365

Asn Asn Gly Lys Thr Val Phe Asp Gly Glu Leu Arg Gln Gly Gln Leu
            370                 375                 380

Leu Val Ile Pro Gln Asn Phe Ala Val Ile Lys Gln Ala Gly Asn Glu
385                 390                 395                 400

Gly Phe Glu Phe Thr Ser Ile Lys Thr Ile Asp Asn Ala Met Val Asn
            405                 410                 415

Thr Ile Val Gly Lys Ala Ser Ala Phe Gln Gly Met Pro Glu Glu Val
            420                 425                 430

Leu Met Asn Ser Tyr Arg Ile Asn Arg Asn Glu Ala Arg Thr Val Lys
            435                 440                 445

Phe Asn Arg Gly His Glu Met Ala Ile Phe Ser Pro Arg Ser Glu Gly
            450                 455                 460

Arg Ala Asp Ala
465

<210> SEQ ID NO 17
<211> LENGTH: 499
<212> TYPE: PRT
<213> ORGANISM: Oryza sativa Japonica Group

<400> SEQUENCE: 17

Met Ala Ser Ile Asn Arg Pro Ile Val Phe Phe Thr Val Cys Leu Phe
1               5                   10                  15

Leu Leu Cys Asp Gly Ser Leu Ala Gln Gln Leu Leu Gly Gln Ser Thr
            20                  25                  30

Ser Gln Trp Gln Ser Ser Arg Arg Gly Ser Pro Arg Gly Cys Arg Phe
            35                  40                  45

Asp Arg Leu Gln Ala Phe Glu Pro Ile Arg Ser Val Arg Ser Gln Ala
```

```
              50                  55                  60
Gly Thr Thr Glu Phe Phe Asp Val Ser Asn Glu Leu Phe Gln Cys Thr
 65                  70                  75                  80

Gly Val Ser Val Val Arg Arg Val Ile Glu Pro Arg Gly Leu Leu Leu
                 85                  90                  95

Pro His Tyr Thr Asn Gly Ala Ser Leu Val Tyr Ile Ile Gln Gly Arg
                100                 105                 110

Gly Ile Thr Gly Pro Thr Phe Pro Gly Cys Pro Glu Thr Tyr Gln Gln
                115                 120                 125

Gln Phe Gln Gln Ser Gly Gln Ala Gln Leu Thr Glu Ser Gln Ser Gln
                130                 135                 140

Ser His Lys Phe Lys Asp Glu His Gln Lys Ile His Arg Phe Arg Gln
145                 150                 155                 160

Gly Asp Val Ile Ala Leu Pro Ala Gly Val Ala His Trp Cys Tyr Asn
                165                 170                 175

Asp Gly Glu Val Pro Val Val Ala Ile Tyr Val Thr Asp Ile Asn Asn
                180                 185                 190

Gly Ala Asn Gln Leu Asp Pro Arg Gln Arg Asp Phe Leu Leu Ala Gly
                195                 200                 205

Asn Lys Arg Asn Pro Gln Ala Tyr Arg Arg Glu Val Glu Glu Trp Ser
210                 215                 220

Gln Asn Ile Phe Ser Gly Phe Ser Thr Glu Leu Leu Ser Glu Ala Phe
225                 230                 235                 240

Gly Ile Ser Asn Gln Val Ala Arg Gln Leu Gln Cys Gln Asn Asp Gln
                245                 250                 255

Arg Gly Glu Ile Val Arg Val Glu Arg Gly Leu Ser Leu Leu Gln Pro
                260                 265                 270

Tyr Ala Ser Leu Gln Glu Gln Gln Gly Gln Met Gln Ser Arg Glu
                275                 280                 285

His Tyr Gln Glu Gly Gly Tyr Gln Gln Ser Gln Tyr Gly Ser Gly Cys
                290                 295                 300

Pro Asn Gly Leu Asp Glu Thr Phe Cys Thr Met Arg Val Arg Gln Asn
305                 310                 315                 320

Ile Asp Asn Pro Asn Arg Ala Asp Thr Tyr Asn Pro Arg Ala Gly Arg
                325                 330                 335

Val Thr Asn Leu Asn Ser Gln Asn Phe Pro Ile Leu Asn Leu Val Gln
                340                 345                 350

Met Ser Ala Val Lys Val Asn Leu Tyr Gln Asn Ala Leu Leu Ser Pro
                355                 360                 365

Phe Trp Asn Ile Asn Ala His Ser Ile Val Tyr Ile Thr Gln Gly Arg
                370                 375                 380

Ala Gln Val Gln Val Val Asn Asn Asn Gly Lys Thr Val Phe Asn Gly
385                 390                 395                 400

Glu Leu Arg Arg Gly Gln Leu Leu Ile Val Pro Gln His Tyr Val Val
                405                 410                 415

Val Lys Lys Ala Gln Arg Glu Gly Cys Ala Tyr Ile Ala Phe Lys Thr
                420                 425                 430

Asn Pro Asn Ser Met Val Ser His Ile Ala Gly Lys Ser Ser Ile Phe
                435                 440                 445

Arg Ala Leu Pro Thr Asp Val Leu Ala Asn Ala Tyr Arg Ile Ser Arg
                450                 455                 460

Glu Glu Ala Gln Arg Leu Lys His Asn Arg Gly Asp Glu Phe Gly Ala
465                 470                 475                 480
```

```
Phe Thr Pro Leu Gln Tyr Lys Ser Tyr Gln Asp Val Tyr Asn Val Ala
                485                 490                 495
Glu Ser Ser

<210> SEQ ID NO 18
<211> LENGTH: 497
<212> TYPE: PRT
<213> ORGANISM: Sesamum indicum

<400> SEQUENCE: 18

Met Ala Leu Thr Ser Leu Leu Ser Phe Phe Ile Val Val Thr Leu Leu
  1               5                  10                  15

Ile Arg Gly Leu Ser Ala Gln Leu Ala Gly Glu Gln Asp Phe Tyr Trp
                 20                  25                  30

Gln Asp Leu Gln Ser Gln Gln His Lys Leu Gln Ala Arg Thr Asp
             35                  40                  45

Cys Arg Val Glu Arg Leu Thr Ala Gln Glu Pro Thr Ile Arg Phe Glu
 50                  55                  60

Ser Glu Ala Gly Leu Thr Glu Phe Trp Asp Arg Asn Asn Gln Gln Phe
 65                  70                  75                  80

Glu Cys Ala Gly Val Ala Ala Val Arg Asn Val Ile Gln Pro Arg Gly
                 85                  90                  95

Leu Leu Leu Pro His Tyr Asn Asn Ala Pro Gln Leu Leu Tyr Val Val
                100                 105                 110

Arg Gly Arg Gly Ile Gln Gly Thr Val Ile Pro Gly Cys Ala Glu Thr
                115                 120                 125

Phe Glu Arg Asp Thr Gln Pro Arg Gln Asp Arg Arg Arg Phe Met
130                 135                 140

Asp Arg His Gln Lys Val Arg Gln Phe Arg Gln Gly Asp Ile Leu Ala
145                 150                 155                 160

Leu Pro Ala Gly Leu Thr Leu Trp Phe Tyr Asn Asn Gly Gly Glu Pro
                165                 170                 175

Leu Ile Thr Val Ala Leu Leu Asp Thr Gly Asn Ala Ala Asn Gln Leu
                180                 185                 190

Asp Gln Thr Phe Arg His Phe Phe Leu Ala Gly Asn Pro Gln Gly Gly
                195                 200                 205

Arg Gln Ser Tyr Phe Gly Arg Pro Gln Thr Glu Lys Gln Gln Gly Glu
                210                 215                 220

Thr Lys Asn Ile Phe Asn Gly Phe Asp Asp Glu Ile Leu Ala Asp Ala
225                 230                 235                 240

Phe Gly Val Asp Val Gln Thr Ala Arg Arg Leu Lys Gly Gln Asp Asp
                245                 250                 255

Leu Arg Gly Arg Ile Val Arg Ala Glu Arg Leu Asp Ile Val Leu Pro
                260                 265                 270

Gly Glu Glu Glu Glu Arg Trp Glu Arg Asp Pro Tyr Ser Gly Ala
                275                 280                 285

Asn Gly Leu Glu Glu Thr Leu Cys Thr Ala Lys Leu Arg Glu Asn Leu
                290                 295                 300

Asp Glu Pro Ala Arg Ala Asp Val Tyr Asn Pro His Gly Gly Arg Ile
305                 310                 315                 320

Ser Ser Leu Asn Ser Leu Thr Leu Pro Val Leu Ser Trp Leu Arg Leu
                325                 330                 335

Ser Ala Glu Lys Gly Val Leu Tyr Arg Asn Gly Leu Val Ala Pro His
                340                 345                 350
```

-continued

```
Trp Asn Leu Asn Ala His Ser Ile Ile Tyr Ile Thr Arg Gly Ser Gly
        355                 360                 365

Arg Phe Gln Val Val Gly His Thr Gly Arg Ser Val Phe Asp Gly Val
    370                 375                 380

Val Arg Glu Gly Gln Leu Ile Ile Val Pro Gln Asn Tyr Val Val Ala
385                 390                 395                 400

Lys Arg Ala Ser Gln Asp Glu Gly Leu Glu Trp Ile Ser Phe Lys Thr
                405                 410                 415

Asn Asp Asn Ala Met Thr Ser Gln Leu Ala Gly Arg Leu Ser Ala Ile
                420                 425                 430

Arg Ala Met Pro Glu Glu Val Val Met Thr Ala Tyr Gln Val Ser Arg
            435                 440                 445

Asp Glu Ala Arg Arg Leu Lys Tyr Asn Arg Glu Glu Ser Arg Val Phe
    450                 455                 460

Ser Ser Thr Ser Arg Tyr Ser Trp Pro Arg Ser Ser Arg Pro Met Ser
465                 470                 475                 480

Tyr Met Pro Lys Pro Phe Glu Tyr Val Leu Asp Val Ile Lys Ser Met
                485                 490                 495

Met

<210> SEQ ID NO 19
<211> LENGTH: 128
<212> TYPE: DNA
<213> ORGANISM: Artificial Sequence
<220> FEATURE:
<223> OTHER INFORMATION: Synthetically generated peptide from Elaeis
      guineensis

<400> SEQUENCE: 19
aagcaatagc cttcagcgtt tctctctttc ttaatttcta aagccatgtc gtccttctct      60
ttgctctcct tttctctttg cttgttgctc ctgtgtcgtg tgtcccaggc tcaatttggg     120
tccagtca                                                             128
```

EXPRESSION REGULATORY ELEMENTS

BACKGROUND OF THE INVENTION

1. Field of the Invention

The present invention relates generally to an expression regulatory element which is operable in plants. More particularly, the present invention provides an expression regulatory element in the form of a promoter operable selectively in endosperm tissue of oil palm plants. Even more particularly, the present invention is directed to the promoter associated with a gene encoding glutelin in endosperm tissue of oil palm plants. The present invention also contemplates other expression regulatory elements, such as enhancers and/or silencers, which are associated with the glutelin gene promoter or are positioned proximal thereto or which otherwise modulate the activity or function of the glutelin gene promoter. The expression regulatory elements of the present invention have utility, inter alia, in the facilitation of tissue specific expression of desired nucleic acid molecules in operable connection thereto which encode, inter alia, RNA which is optionally translated to a peptide, polypeptide or protein. In at least oil palm plants. The expression is tissue specific for the endosperm. Furthermore, the present invention additionally provides a novel isolated glutelin protein and the genetic sequences encoding same.

2. Description of the Prior Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Two different types of storage oil are obtained from oil palm fruits, palm oil from the mesocarp and kernel oil from the kernel. Both oils are different in fatty acid composition, physical properties and usability. Kernel oil is synthesized in the endosperm between 11 and 14 weeks after anthesis (waa). It is rich in medium chain saturated fatty acid namely, 50% lauric acid (C12:0) and 15% myristic acid (C14:0), which serve as important feedstocks for the oleochemical industry. It also contains 15% linoleic acid (C18:2) and lower levels of palmitic acid (C16:0), capric acid (C10:0) and caprylic acid (C8:0), contributing about 7%, 4% and 4%, respectively. Palm kernel meal, the by-product from oil extraction is a valuable animal feed. Oil synthesis in the mesocarp starts later at around 15 waa and stops when the fruits ripen at 20 waa. Palm oil contains 44% palmitic acid (16:0), 5% stearic acid (18:0), 39% oleic acid (18:1) and 10% linoleic acid (18:2). The main applications of palm oil products are in the edible field, however non-food uses such as in cosmetics and as biofuel are advancing.

Being storage tissues, oil palm mesocarp and kernel can be the target for accumulating genetically engineered products without deleterious effects on the plants. It would be highly desirable to manipulate the biochemical pathways for designer oil synthesis in the kernel without affecting mesocarp oil production. The amino acid composition of kernel proteins may also be altered to increase their nutritional values. The kernel would also be suitable target for accumulating high value nutraceuticals and pharmaceuticals by genetic manipulation. To achieve these goals, it is essential to isolate kernel-specific gene promoters and to have an understanding on the regulation of gene expression in the kernel.

Seed storage proteins are synthesized at high levels in the cotyledon and embryo of dicotyledonous plants or in the endosperm of monocotyledonous plants and deposited in protein bodies in the cells of these tissues. The expression of these genes is tightly regulated, thus providing a valuable system for studying molecular mechanisms controlling seed-specific gene expression in higher plants. Seed storage gene promoters have been successfully used for controlling expression of introduced genes to modify oil composition in transgenic oil seed crops. These include utilization of the napin gene promoter for rapeseed (Voelker et al., *Science* 257: 72-73, 1992) and β-conglicinin gene promoter for soybean Kinney, *Journal of Food Lipids* 3: 273-292, 1996). There is also great interest to use promoters from seed storage protein genes to target production of high value novel products to the seeds. The endosperm-specific glutelin gene promoter from rice for example is being used to produce transgenic rice lines with increase level of pro-vitamin A (GoldenRice) (Beyer et al., *Proceedings of the American Society for Nutritional Sciences Symposium on Plant Breeding:* 506S-510S, 2002) and for the production of subunit vaccine in the seeds of transgenic tobacco (Tackaberrry et al., *Genome* 46(3): 521-526, 2003).

Seed storage proteins are classified based on differences of their solubility properties. Saline-insoluble glutelins are found in rice, wheat and other cereals. Glutelins are the major seed storage proteins in rice accounting for more than 80% of the total protein content in the endosperm (Shewry, *Biol. Rev.* 70: 375426, 1995). Typically, seed storage proteins including, glutelin, are encoded by complex multigene families. Sequence analysis revealed that rice glutelins are more closely related to saline-soluble 11S globulins found largely in dicotyledonous species (Muntz, *Plant Molecular Biology* 38: 77-99, 1998). Rice glutelins are synthesized as precursor proteins, which encode an acidic and a basic protein subunit, plus a leader peptide for targeting to the endoplasmic recticulum. The two protein subunits separate post-translationally but subsequently reassociate via formation of disulphide linkages between their cysteine residues. Several polypeptides join together forming an oligomer with suitable conformation to be deposited into protein bodies (Takaiwa et al., *Plant Mol. Biol.* 17(4): 875-885, 1991).

In accordance with the present invention, a tissue-specific expression regulatory element, is identified for endosperm tissue of an oil palm plant, which enables tissue specific expression of nucleic acid molecules associated therewith.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention provides an expression regulatory element operative in plants. In a preferred embodiment, the expression regulatory element is a promoter.

Single pass sequencing of cDNAs from oil palm cDNA libraries, combined with transcript profiling was used to identify genes highly expressed specifically in the kernel of oil palms. Sequence database searching identified one Expressed Sequence Tag (EST) as encoding the seed storage protein glutelin. A genomic clone containing the gene promoter was obtained and fully characterized. The promoter region was identified and the activity of this promoter was analysed via transient assay of reporter gene in oil palm tissue slices. The promoter is selectively operable in endosperm tissue.

The present invention provides, therefore, inter alia, an expression regulatory element associated with gene expression in the endosperm tissue of oil palm plants. The present invention is particularly directed to a regulatory element in the form of a promoter, which is at least specific in oil palm plant endosperm tissue. The present invention extends, however, to other expression regulatory elements associated with expression of nucleic acids such as enhancers or silencers.

Accordingly, one aspect of the present invention contemplates an isolated nucleic acid molecule comprising a tissue-specific expression regulator element, which is tissue specific in oil palm plant endosperm tissue and which facilitates expression of DNA operably connected to said regulatory element in plant cells.

The term "expression regulatory element", as used herein should be understood to refer to any nucleotide sequence which facilitates the expression of a second nucleic acid sequence operably coupled thereto. In a particular embodiment, the expression regulatory element is a promoter. However, as indicated above, enhancers and silencers are also contemplated by the present invention. The term "tissue-specific" when used adjectivally in conjunction with the "expression regulatory element" should be understood to refer to an expression regulatory element which directs expression of a nucleic acid sequence in one or more, but not all, tissues of a plant. It should be noted that although the exemplified expression regulatory elements described herein are endosperm-specific in oil palm plants, in other plant species they may also be endosperm-specific or, alternatively, they may be specific for different tissue(s) or may have a broader spectrum of activity, such as facilitating expression in multiple or all tissues of the plant.

The expression regulatory element described herein is exemplified with respect to the promoter facilitating expression of the gene encoding glutelin in the endosperm of oil palm, although it is contemplated that the expression regulatory elements described herein would be active in a range of plant species. It is proposed to use the expression regulatory elements to facilitate expression of a nucleic acid to generate RNA, mRNA, FRNA, miRNA, siRNA, snRNA, snRNA, stRNA, tRNA, rRNA, snoRNA, imprinting transcripts, anti-sense RNA, sense transcripts. The mRNA may also be further translated into peptides, polypeptides or proteins.

The present invention also contemplates fragments of the expression regulatory element disclosed herein, wherein the fragment retains regulatory activity.

Another aspect of the present invention relates to a recombinant DNA construct, such as a cloning or expression vector, comprising a nucleotide sequence defining an expression regulatory element which is tissue-specific in oil palm plants. Such constructs may optionally further comprise a nucleic acid molecule operably linked to the expression regulatory element and/or means for insertion of such a nucleic acid molecule.

The present invention particularly contemplates a recombinant DNA construct comprising an expression vector which is capable of facilitating expression of a nucleic acid in plant cells, wherein the expression vector comprises an expression regulatory element as described herein in operable connection with a heterologous nucleic acid molecule and wherein the expression regulatory element, at least in oil palm plants, directs specific expression of the heterologous nucleic acid molecule in the endosperm.

The expression vector of the present invention is particularly useful, inter alia, for facilitating expression of a nucleic acid molecule in the endosperm of a plant. Such an expressed nucleic acid molecule may generate products which modify protein or oil qualities; produce or accumulate novel oils or proteins; or the produce or accumulate nutraceuticals, pharmaceuticals, plantibodies and/or other industrial products in the endosperm of the transformed plant.

The present invention further extends to an isolated cell, tissue or organ comprising an expression regulatory element as described herein. Furthermore, the present invention extends to regenerated tissues, organs and whole plants derived from cells, tissues and organs and to propagules and progeny thereof as well as seeds and other reproductive material.

Another aspect of the present invention contemplates methods of identifying binding partners, which bind or otherwise associate with the expression regulatory element hereinbefore described, such methods including electrophoretic mobility assays (gel-shift assays and gel-retardation assays) and DNAase footprinting assays.

In accordance with the present invention, the methods described have particular application for the identification of transcription factors which bind to the expression regulatory elements herein described.

In a related aspect, the present invention contemplates a method for modulating the activity of an expression regulatory element, said method comprising administering to one or more plant cells comprising the expression regulatory element, an agent which binds to the expression regulatory element and modulates the activity of the expression regulatory element. Furthermore, it is contemplated that modulation of the activity of the expression regulatory element would in turn modulate the expression of a nucleic acid molecule in operable connection with the expression regulatory element.

Another aspect of the present invention contemplates a novel glutelin protein and nucleic acid sequences, including both DNA and RNA transcripts thereof encoding same.

A summary of sequence identifiers used throughout the subject specification is provided in Table 1.

TABLE 1

Summary of sequence identifiers

| SEQUENCE ID NO: | DESCRIPTION |
|---|---|
| 1 | Glutelin gene complete ORF sequence |
| 2 | Glutelin amino acid sequence |
| 3 | Glutelin promoter sequence |
| 4 | KRA primer |
| 5 | KA1 primer |
| 6 | KRB primer |
| 7 | KTC primer |
| 8 | KTD primer |
| 9 | GK4 primer |
| 10 | GKN6 primer |
| 11 | GAK5 primer |
| 12 | GAK4 primer |
| 13 | EK1 primer |
| 14 | ANEK2 primer |

A list of abbreviations used herein is provided in Table 2.

TABLE 2

Abbreviations

| ABBREVIATION | DESCRIPTION |
|---|---|
| 2,4-D | 2,4-Dichlorophenoxyacetic acid |
| CaMV | Cauliflower Mosaic Virus |
| EGFP | Enhanced Green Fluorescent Protein |
| EST | Expressed Sequence Tag |
| GFP | Green Fluorescent Protein |
| GUS | β-Glucuronidase |
| NOS | Nopaline Synthase |
| OCS | Octopine Synthase |

TABLE 2-continued

Abbreviations

| ABBREVIATION | DESCRIPTION |
| --- | --- |
| PEG | Polyethylene Glycol |
| scFv | Single Chain Variable Fragment Antibody |
| SCSV | Subclover Stunt Virus |
| waa | weeks after anthesis |

BRIEF DESCRIPTION OF THE FIGURES

FIG. 1 is a graphical representation showing the nucleotide (SEQ ID NO: 1) and deduced amino acid (SEQ ID NO: 2) sequences of a full-length oil palm cDNA clone for the glutelin gene (pOP-KT21). The consensus sequence for the translation start and putative polyadenylation signals are underlined.

FIG. 2 is a tabular representation summarizing percentages of identity at the nucleotide and amino acid levels between sequences of the different glutelin genes from oil palm FIG. 3 is a graphical representation showing a multiple sequence alignment for the deduced amino acid sequences of three oil palm glutelin genes [pOP-KT21 (SEQ ID NO: pKT7 (AF261691; SEQ ID NO: 16) and pKT9 (AF193433; SEQ ID NO: 15)], rice glutelin gene (P07730; SEQ ID NO: 17) and sesame 11S globulin gene (AF240004; SEQ ID NO: 18). Asterisks represent identical amino acids. Colons indicate conservation of strong groups and dots indicate conservation of weak groups. Putative cleavage sites for signal peptide and for separating the acidic and basic protein subunits are indicated by downward arrows. Conserved cysteine residues are indicated by ♦.

FIG. 4 is a tabular representation showing a comparison between the amino acid profiles of the deduced amino acid sequence of pOP-KT21 and palm kernel meal. (A) is the amino acid usage in the deduced amino acid sequence of pOP-KT21, (B) is the amino acid composition of palm kernel meal.

FIG. 8 is a photomicrographic representation showing the cell-specific expression pattern of glutelin genes in the endosperm tissue of the oil palm RNA in situ hybridization of kernel section of oil palm fruits using DIG-labelled RNA probes coding for oil palm glutelin (pOP-KT21) visualizing using Leica Q550FW Imaging Microscope System. PANEL (a): A sense RNA probe was used on a 5 μm thick section (magnification 33×). PANEL (b): An antisense RNA probe was used on 5 μm thick section (magnification 33×)

FIG. 10 is a graphical representation showing the sequence of the oil palm glutelin gene (pOP-KT21) promoter (SEQ ID NO: 3). This promoter is found in the oil palm genomic clone pKT21-Pa and was isolated by genome walking. In the promoter sequence, the putative expression regulatory elements (Skn-1-like and AACA motifs), TATA box and the adenine at the 5' end of the 5' RACE product (likely transcription start site) are underlined.

FIG. 11 is a graphical representation showing a DNA sequence alignment of pKT21-Pa (genomic sequence; SEQ ID NO: 19) and pOP-KT21 (cDNA sequence; SEQ ID NO: 1). Alignment of pKT21-Pa sequence and the sequence of pOP-KT21 (nucleotides 1-128) clearly showing 100% homology within the overlapping region.

FIG. 13 is a tabular representation showing optimized bombardment parameters for transient assay analysis using oil palm kernel tissue slices.

FIG. 15 is a tabular representation showing counts of GFP spots in leaf, mesocarp and kernel tissues bombarded with GluP-EGFP, CaMV-EGFP (positive control) and pEGFP control (negative control); average of 3 independent experiments

DETAILED DESCRIPTION OF THE INVENTION

Figure 5:
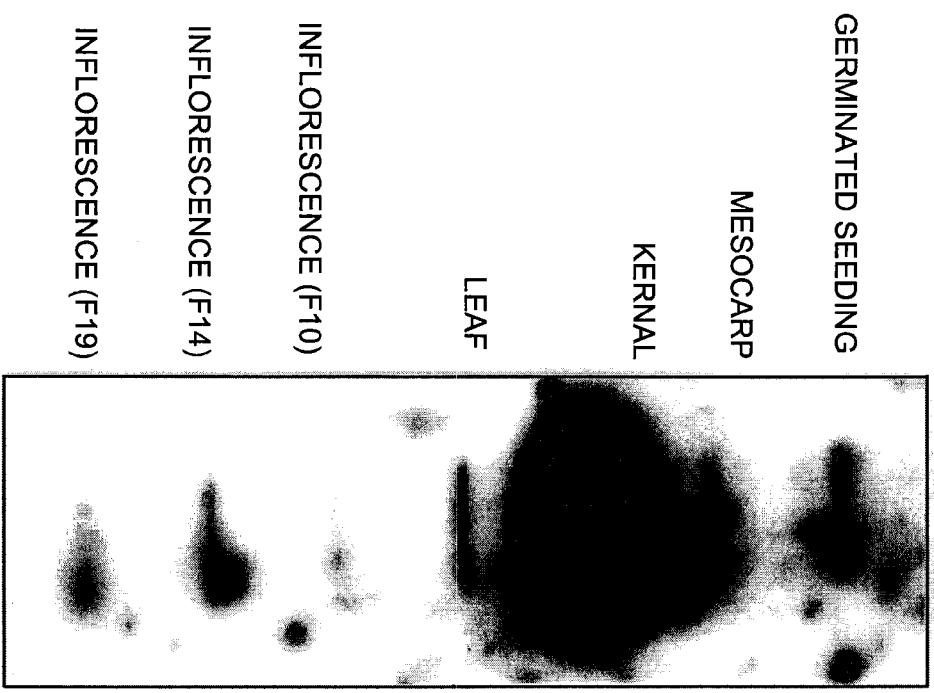
FIG. 5 is a graphical representation showing the expression pattern of the glutelin genes (subfamily B) in different oil palm tissues. Slot blot containing 1 g poly (A)⁻ RNA from various oil palm (*E. guineensis*) tissues, as indicated, was hybridised with $^{32}$P-labelled probe prepared from pOP-KT21 EST.

The present invention is predicated, in part, on an expression regulatory element which is tissue specific in oil palm plants. Conveniently, the expression regulatory element directs or facilitates expression of a gene encoding glutelin in the endosperm of oil palm plants. Isolation of this expression regulatory element permits, inter alia, the expression of nucleic acid molecules in operable connection with the expression regulatory element, which at least in oil palm plants will be tissue-specific in the endosperm. In other plant species expression may also be endosperm-specific or, alternatively, expression may be specific for different tissue(s) or may have a broader spectrum of activity, such as facilitating expression in multiple or all tissues of the plant.

Before describing the present invention in detail, it is to be understood that unless otherwise indicated, terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "an expression regulatory element" includes a single element, as well as two or more elements or a combination of elements. For example, "an expression regulatory element" may comprise a single promoter region, multiple promoter regions, or one or more promoter regions together with other expression regulatory elements such as enhancers or silencers. Accordingly, one aspect of the present invention contemplates an isolated nucleic acid molecule comprising a tissue-specific expression regulatory element, which is tissue specific in oil palm plant endosperm tissue and which facilitates expression of DNA operably connected to said regulatory element in plant cells.

The term "expression regulatory element", as used herein should be understood to refer to any nucleotide sequence which facilitates the expression of a second nucleic acid sequence operably coupled thereto. In a particular embodiment, the expression regulator, element is a promoter. However, as indicated above, enhancers and silencers are also contemplated by the present invention. The term "tissue-specific" when used adjectivally in conjunction with the "expression regulatory element" should be understood to refer to an expression regulatory element which directs expression of a nucleic acid sequence in one or more, but not all, tissues of a plant. It should be noted that although the exemplified expression regulator) elements described herein are endosperm-specific in oil palm plants, in other plant species they may also be endosperm-specific or, alternatively, they may be specific for different tissue(s) or may have a broader spectrum of activity, such as facilitating expression in multiple or all tissues of the plant.

A "promoter" is defined as any nucleic acid sequence which facilitates expression of a second nucleic acid molecule operably connected thereto.

In a preferred embodiment of the present invention, the expression regulatory element is a promoter.

The present invention, however, also extends to other expression regulatory elements such as an enhancer or silencer.

An "enhancer" binds transcription factors known as "enhancer binding proteins", which may also bind to the promoter of a gene. Binding of an enhancer and promoter to a transcription factor brings the two regions into association, which then affects the activity of the promoter and enhances the rate of transcription of any operably connected gene.

"Silencers" are control regions of DNA that, like enhancers, bind transcription factors. However, in contrast to enhancers, when transcription factors bind to a silencer, expression of the gene they control is repressed.

The expression regulatory element of the present invention was isolated from upstream of the glutelin encoding gene in the oil palm. Glutelin is, a seed storage protein that accumulates in the endosperm of monocotyledenous plants. "Endosperm" is the name given the nutrient-rich triploid tissue comprised of parenchyma cells, which surrounds the embryo in plant seeds. In oil palm, the endosperm may be interchangeably referred to as the "kernel". The present invention has identified the promoter of the glutelin gene in oil palm, and identified that this promoter leads to endosperm-specific expression of a nucleic acid molecule operably coupled thereto. The present invention contemplates, inter alia, the use of the characteristics of this promoter to specifically express transgenes in the endosperm of transgenic plants. It is contemplated that re-direction of the metabolic flux toward the production of a heterologous product in storage tissue, such as the endosperm, should be possible with little metabolic cost to the plant in terms of growth and vigour. As used herein, the term "oil palm" should be understood to refer oil palm plants such as the species *E. guineensis* and *E. oleifera* including modified varieties or genetic variants thereof.

The tissue-specific expression regulatory element described herein is exemplified with respect to the promoter facilitating expression of the gene encoding glutelin in the endosperm of oil palm, although it is contemplated that the expression regulatory elements described herein would be active in a range of plant species with respect to facilitating expression of range of operably connected nucleic acid molecules. Examples of such nucleic acid molecules include DNA sequences which are transcribed into either coding RNA such as mRNA which is further translated into peptides, polypeptides or proteins; and DNA which is transcribed into a non-protein-coding RNA (ncRNA), which includes, but is not limited to PNA, miRNA, siRNA, snRNA, snmRNA, stRNA, tRNA, rRNA, snoRNA, imprinting transcripts, sense RNA, antisense RNA and the like. More particularly, the present invention is directed to a nucleic acid molecule or derivative or homolog thereof comprising a nucleotide sequence encoding a expression regulatory element, wherein the nucleotide sequence is as set forth in SEQ ID NO:3 or a nucleotide sequence having at least about 50% identity to SEQ ID NO:3 after optimal alignment or a nucleotide sequence capable of hybridizing to SEQ ID NO:3 or it's complementary form under low stringency conditions.

The term "similarity," as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and amino acid sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (ie. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT. FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 5: 3389-3402, 1997). A detailed discussion of sequence analysis can be found in Unit 19.3 of Ausubel et al., ("Current Protocols in Molecular Biology" John Wiley & Sons Inc, 1994-1998, Chapter 15, 1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, H is, Asp, Glu, Asn, Gin, Cys and Met) occurs in both sequences to yield the number of matched positions, dividing the number of matched positions by the total number of positions in the window of comparison (ie., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd. South San Francisco, Calif., USA) using standard defaults as used in the reference manual accompanying the software. Similar comments apply in relation to sequence similarity. The term "similarity" is particularly useful to describe amino acid sequence comparisons. The term "identity" is particularly useful to describe nucleotide sequence comparisons.

Reference to greater than 50% identity or similarity includes percentage identities and similarities greater than 50% such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

Preferably, the expression regulatory element comprises an isolated nucleic acid molecule of comprising the nucleic acid sequence as set forth in SEQ ID NO:3.

The present invention also contemplates mutants and derivatives of the expression regulatory element or of DNA comprising the expression regulatory element, and in particular those mutants or fragments which retain activity. For example, an expression regulatory element may comprise a promoter and enhancer element, which may be separated into separate fragments, both of which would fall within the scope of the present invention. Furthermore, the expression regulatory element of the present invention may be subjected to deletion analysis to determine the minimal functional fragment need to drive gene expression in parenchyma cells, or in the endosperm tissue. Alternatively, such deletion mutants may have increased or decreased activity by the deletion of enhancer or silencer regions within the expression regulatory element. Such expression regulatory elements are also contemplated by the present invention.

Another aspect of the present invention relates to recombinant DNA constructs comprising a nucleotide sequence comprising the expression regulatory element or a fragment thereof as described herein.

"Recombinant DNA constructs" contemplated by the present invention include any isolated nucleic acid molecule comprising the expression regulatory element. Particularly useful recombinant DNA constructs include vectors, such as cloning vectors and expression vectors.

The term "vectors" as used herein refers to construct used for the purpose of multiplying, propagating, transferring a nucleic acid from one organism to another (eg. cloning vectors) or for the expression of a nucleic acid (which may optionally encode a protein) in a cell (expression vectors). As will be readily ascertained by one of skill in the art, in some cases, depending on the nucleic acid molecule of interest, a vector may comprise both a cloning vector and an expression vector. For example, a cloning vector with an expressed selectable marker would be a cloning vector with regard to the cloned nucleic acid, but an expression vector with regard to the selectable marker gene. Particularly useful vectors include: plasmid vectors, viral vectors, transposon vectors, cosmids and artificial chromosomes (including bacterial artificial chromosomes and yeast artificial chromosomes). Other vectors would be readily apparent to one of skill in the art, and the present invention is in no way limited by the vector types listed above.

Accordingly, another aspect of the present invention contemplates a vector comprising a nucleic acid of the present invention as hereinbefore described.

In a preferred embodiment the vector is an expression vector which is capable of facilitating expression of a nucleic acid in plant cells, wherein the expression vector comprises an expression regulatory element as described herein in operable connection with a heterologous nucleic acid molecule and wherein the expression regulatory element, at least in oil palm plants, directs specific expression of the heterologous nucleic acid molecule in the endosperm.

Placing a nucleic acid molecule under the operable control of an expression regulatory element, such as a promoter, means positioning the molecule such that expression is controlled by the expression regulatory element. For example, promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting. i.e. the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e. the genes from which it is derived. Again, as is known in the art some variation in this distance can also occur.

The construct or vector preferably contains additional expression regulatory elements for efficient transcription, for example, a transcription termination sequence.

The term "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo.

The terminator may be any terminator sequence which is operable in the cells, tissues or organs in which it is intended to be used.

Examples of terminators particularly suitable for use in the synthetic genes of the present invention include the SV40 polyadenylation signal, the HSV TX polyadenylation signal, the CYC1 terminator, ADH terminator, SPA terminator, nopaline synthase (NOS) gene terminator of *Agrobacierium tumefaciens*, the terminator of the cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is octopine synthase (OCS) or nopaline synthase (NOS) terminator which is active in plant cells, tissue or organs.

Those skilled in the art will be aware of additional terminator sequences which may be suitable for use in performing the invention. Such sequences may readily be used without any undue experimentation.

The constructs described supra are capable of being modified further, for example, by the inclusion of marker nucleotide sequences encoding a detectable marker enzyme or a functional analogue or derivative thereof, to facilitate detection of the synthetic gene in a cell, tissue or organ in which it is expressed. According to this embodiment the marker nucleotide sequences till be present in a translatable format and expressed.

Those skilled in the art will be aware of how to produce the constructs described herein and of the requirements for obtaining the expression thereof. In particular, it will be known to those skilled in the art that the genetic manipulations required to perform the present invention may require the propagation of a genetic construct described herein or a derivative thereof in a prokaryotic cell such as an *E. coli* or *Agrobacierium sp.* cell or a plant cell or an animal cell.

To produce a genetic construct, a nucleic acid is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly, a further aspect of the invention provides a genetic construct which comprises, inter alia, an expression regulatory element as herein described and optionally one or more origins of replication and/or selectable marker gene sequences.

Typically, an origin of replication or a selectable marker gene suitable for use in bacteria is physically-separated from those genetic sequences contained in the genetic construct which are intended to be expressed or transferred to a plant cell, or integrated into the genome of a plant cell.

As used herein, the term "selectable marker gene" includes any gene which confers a phenotype on a cell on which it is expressed to facilitate the identification and/or selection of cells which are transfected or transformed with a genetic construct of the invention or a derivative thereof.

Suitable selectable marker genes contemplated herein include the ampicillin-resistance gene ($Amp^r$), tetracycline-resistance gene ($Tc^r$), bacterial kanamycin-resistance gene ($Kan^r$), the zeocin resistance gene (Zeocin is a drug of the bleomycin family which is trade mark of InVitrogen Corporation), the AURI-C gene which confers resistance to the antibiotic aureobasidin A, phosphinothricin-resistance gene, neomycin phosphotransferase gen (nptII), hygromycin-resistance gene, β-glucuronidasc (GUS) gene, chloramphenicol acetyltransferase (CAT) gene, green fluorescent protein-encoding gene or the luciferase gene, amongst others.

Preferably, the selectable marker gene is the nptII gene or $Kan^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as described herein, which include further genetic sequences intended for the maintenance and/or replication of said genetic construct in prokaryotes or eukaryotes and/or the integration of said genetic construct or a part thereof into the genome of a eukaryotic cell or organism.

Another aspect of the present invention contemplates a method for expressing a nucleic acid molecule in a transgenic plant, said method comprising transforming a plant, plant cell, plant tissue or plant organ, with the vector described herein and regenerating the transformed plant.

Preferably, the nucleic acid molecule is specifically expressed in the endosperm of the transformed plant or tissue.

Standard methods may be used to introduce the constructs into the cell, tissue or organ, for example, liposome-mediated transfection or transformation, transformation of cells with attenuated virus particles or bacterial cells, cell mating, transformation or transfection procedures known to those skilled in the art.

Particularly useful means for introducing recombinant DNA into plant tissue or cells include, but are not limited to, microparticle bombardment of tissue explant or cells, transformation using $CaCl_2$ and variations thereof direct DNA uptake into protoplasts, PEG-mediated uptake to protoplasts, electroporation, microinjection of DNA, vacuum-infiltration of tissue with a nucleic acid and T-DNA-mediated transfer from *Agrobacierium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

For Agrobacterium-mediated transformation, the construct itself may comprise sequences necessary to facilitate its own transfer into plant tissue, for example it may comprise a region encoding the vir genes from the Ti plasmid. Typically, these vectors are constructed by homologous recombination between a disarmed Agrobacterium Ti plasmid (ie. one which has had the tumorigenic regions of the T-DNA knocked out) and a construct containing the gene of interest and a region of homology with the disarmed Ti plasmid. A vector of this type is referred to as a "co-integrated vector". However, the vir region may also be present on a separate construct to the gene to be transferred, known as a binary vector system. In this case the genes to be transferred (typically at least the gene of interest and a selectable marker) are flanked by the T-DNA border regions from a Ti plasmid on one construct. Furthermore in the Agrobacterium donor, a second construct must be present that comprises the vir region of the Ti plasmid, and supplies the transfer mechanism in traits. Typically this vii-encoding construct has no T-DNA region, and no part of this "helper" construct is transferred. In addition to these essential features, it will be readily apparent to one of skill in the art that the constructs described above may further include other features such as but not limited to: bacterial origins of replication; bacterial transfer genes such as mob; selectable marker genes and the like.

In a further embodiment of the present invention, the genetic constructs described herein are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the Agrobacterium tumefaciens Ti plasmid will generally be required.

Plants may be regenerated from transformed plant cells or tissues or organs on hormone-containing or hormone-free regeneration media and the regenerated plants may take a variety of forms, such as chimeras of transformed cells and non-transformed cells: clonal transformants (eg. all cells transformed to contain the expression cassette); grafts of transformed and untransformed tissue (eg. a transformed root stock grafted to an untransformed scion in citrus species). Transformed plants may be propagated by a variety of means, such as by clonal propagation or classical breeding techniques. For example, a first generation (or T1) transformed plants may be selfed to give homozygous second generation (or T2) transformed plants, and the T2 plants further propagated through classical breeding techniques.

The methods contemplated by this aspect of the present invention, although applicable to any plant species, are particularly useful for plants selected from the list species consisting of: *Elaeis guineenis* Jacq. *Elaeis oleifera* and their hybrids; maize, rice, soybean, tobacco, cotton, alfalfa, wheat, *Arabidopsis*, rapeseed, canola and coconut.

In a particularly preferred embodiment, the methods of the present invention are used to transform *Elaeis* spp. with a nucleic acid which, when expressed, effects:
 (i) modification of protein or oil qualities:
 (ii) production or accumulation of novel oils or proteins; or
 (iii) the production or accumulation of nutraceuticals, pharmaceuticals and/or other industrial products;
 (iv) production of plantibodies;
in the endosperm of the transformed plant. It is contemplated that the expression of a transgene under the operable control of the expression regulatory element of the present invention will be substantially limited to the endosperm of the plant such that metabolism in other parts of the plant, including oil accumulation in the mesocarp, will not be affected.

It should also be noted that the methods, expression regulatory elements and constructs of the present invention may be equivalently applied for the expression of a nucleic acid a plant other than an oil palm (*Elaeis* spp.). Accordingly, the present invention is in no way limited to relating to only *Elaeis* spp. plants, and the methods, expression regulatory elements and constructs of the present invention are applicable to any plant.

One particularly useful method for modification of the oil content of the endosperm involves the expression of a nucleic acid molecule that affects fatty acid biosynthesis or accumulation. Examples of such nucleic acids include nucleic acids encoding fatty acid biosynthetic enzymes and antisense nucleic acids (including DNA and RNAi) to fatty acid biosynthetic genes.

Examples of accumulation of storage oils include increase in levels of medium chain fatty acids including lauric acid and myristic acid or C18:1 oleic acid for applications in oleochemical industry. This would involve genetic manipulation of genes encoding enzymes in the plant fatty acid biosynthetic pathway such as acyl-ACP thioesterase (fatA and fatB), acetyl-CoA carboxylase, β-ketoacyl-ACP synthase (KASI, KAS II, KASIII and KAS IV). One or a combination of genes may be manipulated to produce oil with the desired fatty acid composition.

Examples of accumulation nutraceuticals or pharmaceuticals that are contemplated by the present invention include:
 (i) pro-vitamin A accumulation;
 (ii) accumulation or biosynthesis of iron-inch compounds;
 (iii) biosynthesis or accumulation of antigenic peptides for use as oral vaccines.

Palm kernel meal is commonly used as an animal feed. Accordingly, the present invention contemplates a method producing a genetically modified plant with altered amino acid composition or oil composition in the kernel, such that the kernel has a greater nutritional value when compared to wild type oil palm kernel.

One example of the alteration of the nutritional value of palm kernel meal is expression of a protein in the endosperm which contains increased levels of one or more of the "essential" amino acids for mammals, or contains balanced levels of all the essential amino acids for mammals.

Prokaryotes such as *E. coli* can make the carbon skeletons of all 20 amino acids and transaminate those carbon skeletons with nitrogen from glutamine or glutamate to complete the amino acid structures. Humans cannot synthesize the branched carbon chains found in branched chain amino acids or the ring systems found in phenylalanine and the aromatic amino acids; nor can humans incorporate sulfur into covalently bonded structures. Therefore, the 10 so-called essential amino acids (see Table 3) must be supplied from the diet. Nevertheless, it should be recognized that, depending on the composition of the diet and physiological state of an individual, one or another of the non-essential amino acids may also become a required dietary component. For example, arginine is only normally considered to be essential amino acid during early childhood development because enough for adult needs is made by the urea cycle.

To take a different type of example, cysteine and tyrosine are considered non-essential but are formed from the essential amino acids methionine and phenylalanine, respectively. If sufficient cysteine and tyrosine are present in the diet, the requirements for methionine and phenylalanine are markedly reduced; conversely, if methionine and phenyl alanine are present in only limited quantities, cysteine and tyrosine can become essential dietary components. Finally, it should be recognized that if the α-keto acids corresponding to the carbon skeletons of the essential amino acids are supplied in the diet, aminotransferases in the body will convert the keto acids to their respective amino acids, largely supplying the basic needs.

Unlike fats and carbohydrates, nitrogen has no designated storage depots in the body. Since the half-life of many proteins is short (on the order of hours), insufficient dietary quantities of even one amino acid can quickly limit the synthesis and lower the body levels of many essential proteins. The result of limited synthesis and normal rates of protein degradation is that the balance of nitrogen intake and nitrogen excretion is rapidly and significantly altered. Normal, health) adults are generally in nitrogen balance, with intake and excretion being very well matched. Young growing children, adults recovering from major illness, and pregnant women are often in positive nitrogen balance. Their intake of nitrogen exceeds their loss as net protein synthesis proceeds. When more nitrogen is excreted than is incorporated into the body, an individual is in negative nitrogen balance. Insufficient quantities of even one essential amino acid is adequate to turn an otherwise normal individual into one with a negative nitrogen balance.

The biological value of dietary proteins is related to the extent to which they provide all the necessary amino acids. Proteins of animal origin generally have a high biological value; plant proteins have a wide range of values from almost none to quite high. In general, plant proteins are deficient in lysine, methionine, and tryptophan and are much less concentrated and less digestible than animal proteins. The absence of lysine in low-grade cereal proteins used as a dietary mainstay in many underdeveloped countries, leads to an inability to synthesize protein (because of missing essential amino acids) and ultimately to a syndrome known as kwashiorkor, common among children in these countries.

Accordingly, the present invention contemplates a method for increasing the nutritional value of palm kernel meal, by expression of one or more nucleic acids under the control of the expression regulatory element described herein, wherein the nucleic acid encodes a protein with increased levels of one or more essential amino acids when compared the wild type oil palm glutelin protein.

In preferred embodiments, the nucleic acid encodes a protein with increased levels of one or more of lysine, methionine and tryptophan when compared to the wild type oil palm glutelin protein.

TABLE 3

Essential vs. Nonessential Amino Acids

| Nonessential | Essential |
|---|---|
| Alanine | Arginine* |
| Asparagine | Histidine |
| Aspartate | Isoleucine |
| Cysteine | Leucine |

TABLE 3-continued

Essential vs. Nonessential Amino Acids

| Nonessential | Essential |
|---|---|
| Glutamate | Lysine |
| Glutamine | Methionine* |
| Glycine | Phenylalanine* |
| Proline | Threonine |
| Serine | Tyrptophan |
| Tyrosine | Valine |

*The amino acids arginine, methionine and phenylalanine are considered essential for reasons not directly related to lack of synthesis. Arginine is synthesized by mammalian cells but at a rate that is insufficient to meet the growth needs of the body and the majority that is synthesized is cleaved to form urea. Methionine is required in large amounts to produce cysteine if the latter amino acid is not adequately supplied in the diet. Similarly, phenylalanine is needed in large amounts to form tyrosine if the latter is not adequately supplied in the diet.

In a further preferred embodiment, the nucleic acid molecule operably linked to the expression regulatory element encodes a plantibody. Plantibodies are Human or other animal antibodies produced by, and in, transgenic plants. Plantibodies are produced in transgenic plants by the expression of a nucleic acid encoding a humanized antibody.

As used herein, the term "plantibody" should be understood to encompass any complete antibody, including single chain antibodies such as single chain variable fragment (scFv) antibodies, multiple chain antibodies and monomers thereof, which are produced in a plant. Monomers of antibodies contemplated by the present invention include, for example, light and heavy chains of mammalian antibodies. The "plantibody" produced by the present invention need not be produced in a functional form by the plant to be encompassed by die present invention. For example, the invention specifically contemplates the production of one chain or monomer of a multimeric antibody in a plant, which may then be later complexed with other chains or monomers to produce a functional multimeric antibody. The present invention also contemplates transformation of two or more plants with different constructs encoding distinct, but complementary antibody chains, such that when the plants are crossed the offspring may inherit each of the antibody-chain-encoding genes from each parent and then be able to produce a functional antibody/plantibody. Production of an antibody in a plant as a plantibody can be far more efficient in terms of antibody production when compared to mammalian cell culture. For example, a 10000 liter mammalian cell culture typically yields one or two kilograms of usable antibodies. In contrast, plantibodies have been produced at yields of about 1.5 kilograms of pharmaceutical-quality antibodies per acre of corn.

Plantibodies may also reduce the risk of contamination, as plants are not susceptible to human diseases like mammalian cell cultures are. Although it must be ensured that plantibodies are free from pesticides and other kinds of contaminants, screening for viruses and bacterial toxins may be substantially reduced.

Several plant species have been used in the art to produce plantibodies, and some examples are indicated in Table 4.

TABLE 4

Therapeutic and diagnostic plantibodies

| Application and specificity | Signal sequences | Antibody name or type | Plant |
|---|---|---|---|
| Dental caries; streptococcal | Murine IgG signal peptides | Guy's 13 (Secretory IgA) | *Nicotiana Tabacum* |
| Diagnostic; anti-human IgG | Murine IgG signal peptides | C5-1 (IgG) | alfalfa |

TABLE 4-continued

Therapeutic and diagnostic plantibodies

| Application and specificity | Signal sequences | Antibody name or type | Plant |
|---|---|---|---|
| Cancer treatment; carcinoembryonic antigen | Murine IgG signal peptide; KDEL | ScFvT84.66 (ScFv) | *Triticum aestivum* |
| Cancer treatment; carcinoembryonic antigen | Murine IgG signal peptide; KDEL | ScFvT84.66 (ScFv) | rice |
| Cancer treatment; carcinoembryonic antigen | TMV leader; murine IgG signal peptides; KDEL | T84.66 (IgG) | *Nicotiana tabaccum* (transient expression with *Agrobacterium* infiltration) |
| B-cell lymphoma treatment; idiotype vaccine | Rice α-amylase | 38C13 (scFv) | *Nicotiana Benthamiana* |
| Colon cancer; surface antigen | Murine IgG signal peptide; KDEL | CO17-1A (IgG) | *Nicotiana Benthamiana* |
| Herpes simplex virus 2 | Tobacco extensin signal peptide | Anti-HSV-2 (IgG) | soybean |

(Daniell et al., Trends in Plant Science 6(5): 219-226, 2001)

Methods for effecting the expression of an antibody-encoding gene in a plant would be well known to those of skill in the art. However, an outline of the steps typically undertaken to produce a plantibody are shown below:
  (i) Identification and characterization of a target human monoclonal antibody using transgenic mouse systems, a phage display library or by humanization of mouse antibodies.
  (ii) Insertion of the antibody genes into a DNA vector that alloys expression in a whole plant or a specific part of the plant by one of several well-established techniques, such as biolistic delivery, *Agrobacierium*-mediated transformation, electroporation and the like.
  (iii) Regeneration of whole plants from transformed plant cells.
  (iv) Purification of human monoclonal antibody from plant tissue.

Typically, production of a plantibody uses the procedure described supra, however, it should be understood that the present invention is in no way limited to any one method for the production of plantibodies.

Accordingly, the present invention contemplates a method for the specific production of a plantibody, in the endosperm of a plant, said method comprising transforming a plant with a recombinant DNA construct comprising a nucleic acid encoding an antibody in operable connection with the expression regulatory element described herein.

Other nucleic acid molecules for which tissue specific expression facilitated by the expression regulatory elements described herein would be desirable, would be readily ascertained by one of skill in the art. However, examples of nucleic acid molecules for which it would be desirable to have endosperm-specific expression include nucleic acids encoding one or more biosynthetic enzymes, or antisense transcripts thereof which would cause the accumulation or reduction in the amount of a metabolite in the endosperm of the transformed plant. Some examples of such genes encoding biosynthetic enzymes include, but in no way limit the invention:
  (i) vanillin biosynthetic enzymes, including 3-dehydroshikimate dehydratase, catechol-o-methyltransferase, aryl aldehyde dehdrogenase, feruloyl-CoA synthetase, enoyl-CoA hydratase/aldolase;
  (ii) sorbitol biosynthetic enzymes, including glucose/fructose oxidoreductase;
  (iii) PHA biosynthetic enzymes, including 3-ketothiolase, acetoacetyl-CoA reductase, PHA synthase, enoyl hydratase, 3-hydroxyacyl-acyl carrier protein: CoA tranferase;
  (iv) indigo biosynthetic enzymes, including tryptophanase, L-tryptophan indole lyase, napthalene dioxygenase, *R. eutrophica bec* gene product;
  (v) fructan biosynthetic enzymes, including fructosyltransferases aid levansucrases;
  (vi) lactic acid biosynthetic enzymes, including lactate dehydrogenase;
  (vii) adipic acid biosynthetic enzymes, including 3-dehydroshikimate dehydratase, protocatechuate decarboxylase and catechol 1:2-dioxygenase:
  (viii) petroselinic acid biosynthetic enzymes, including 3-ketoacyl-ACP synthase;
  (ix) 1,3-propanediol biosynthetic enzymes including glycerol dehydratase, 1,3-propanediol oxidoreductase, glycerol-3-phosphate dehydrogenase, and glycerol-3-phosphatase; and/or
  (x) 2-phenylethanol biosynthetic enzymes including aromatic-L-amino acid decarboxylase, 2-phenylethylamine oxidase and aryl alcohol dehydrogenase.
  (xi) pHBA biosynthetic enzymes including 4-hydroxycinnamoyl-CoA hydratas/lyase (HCHL) and chorismate pyruvate lyase (CPL).

The present invention further extends to an isolated cell, tissue or organ comprising the expression regulatory element as described herein. Furthermore, the present invention extends further to regenerated tissues, organs and whole organisms derived from said cells, tissues and organs and to propagules and progeny thereof as Novell as seeds and other reproductive material.

Preferably, the cell, tissue, organ or organism is a plant cell, plant tissue, plant organ or plant.

The term "reproductive material" as used herein is to be understood as any plant seed, tissue, cutting, explant, cell or pollen that may be used to:
  (i) propagate the plant via sexual reproduction;
  (ii) propagate the plant via vegetative propagation; or
  (iii) generate a plant cell or tissue culture of the plant and/or regenerate a plant from the culture.

Examples of reproductive material contemplated by the present invention includes: but are in no way limited to: seeds, fruits, cones, cuttings, explants, cells, anthers, pollen, flowers (including parts thereof), tubers, bulbs, callus tissue, embryogenic callus, suspension cultures and embryos (including immature embryos).

Preferably, the transgenic plant cell, or plant, tissue, organ or plant part comprising one or more of said cells, is from the list species consisting of: *Elaeis guineensis* Jacq., *Elaeis oleifera* and their hybrids; maize, rice, soybean, tobacco, cotton, alfalfa, wheat, *Arabidopsis*, rapeseed, canola and coconut.

Another aspect of the present invention contemplates a method of identifying binding partners, which bind or otherwise associate with the expression regulatory element hereinbefore described.

Particularly preferred methods for assessing binding between a DNA molecule (such as the expression regulatory elements of the present invention) and a binding partner include electrophoretic mobility assays (gel-shift assays and gel-retardation assays) and DNAase footprinting assays. These assays would be well known to those of skill in the art.

Briefly, electrophoretic mobility shift assays involve contacting a putative binding partner with the nucleic acid molecule of interest (eg. an expression regulatory element of the present invention), said contact under such conditions and for a time to allow binding to occur. Binding between the putative binding partner and the nucleic acid molecule is determined by the electrophoretic mobility of the putative nucleic acid/binding partner complex A reduction in electrophoretic mobility of the nucleic acid molecule of interest when in complex with the putative binding partner is indicative of binding between the putative binding partner and the nucleic acid molecule.

Electrophoretic mobility assays have utility for the detection of a range of DNA binding agents including other nucleic acids (eg. DNA and RNA) and proteins.

DNAase footprinting assays utilize the activity of DNAase I. DNAase I in the presence of $Mg^{2+}$, hydrolyzes each strand of DNA independently in a statistically random fashion. This property of the nuclease is useful in the analysis of DNA-protein complexes. Regions of DNA which have bound proteins are protected from the attack of properly diluted DNAase 1. Therefore, after digestion with DNAaseI regions of the DNA protected by a bound protein can be isolated and sequenced. Full details of such assays are described by Galas and Schmitz (*Nucl. Acids Res.* 5: 3157-3170, 1978). Accordingly, this method may be used to identify binding agents of the expression regulatory elements of the present invention by contacting a putative binding agent with the a nucleic acid comprising a sequence of nucleotides encoding a expression regulatory element described herein for a time and under conditions to allow binding; digesting the putative complex with appropriately diluted DNAase r to digest the DNA not protected by bound protein; and identification of a putative binding agent as a binding agent of the nucleic acid by the detection of an undigested, ie. protected, region of the nucleic acid molecule.

The present invention further extends to other methods known to those of skill in the art which utilize the nucleic acid molecules provided by the present invention, or the sequence information derived therefrom, to identify binding agents of the expression regulatory elements described herein.

In accordance with the present invention, the methods described have particular application for the identification of transcription factors which bind to the expression regulatory elements described herein.

The term "transcription factor" as used herein refers to any agent which regulates the expression of a gene by binding to one or more regions within the expression regulatory element of that gene. As such a transcription factor may bind to one or more promoter, enhancer or silencer regions for a particular gene. Transcription factors most commonly are proteins, but may also be co-enzymes, vitamins or other organic molecules. It should be understood that the present invention is in no way limited by the nature of any transcription factor itself, which is identified in accordance with the present invention.

The present invention further extends to transcription factors and other agents which bind to the expression regulatory element described herein, when identified in accordance with the present invention.

In a related aspect, the present invention contemplates a method for modulating the activity of an expression regulatory element, said method comprising administering to one or more plant cells comprising the expression regulatory element, an agent which binds to the expression regulatory element and modulates the activity of the expression regulatory element. Furthermore, it is contemplated that modulation of the activity of the expression regulatory element would in turn modulate the expression of a nucleic acid molecule in operable connection with the expression regulatory element.

Finally, another aspect of the present invention provides an isolated nucleic acid molecule comprising a sequence of nucleotides, wherein the nucleotide sequence encodes a glutelin protein comprising the amino acid sequence set forth in SEQ ID NO:2 or an amino acid sequence having greater than 92% similarity to SEQ ID NO:2 after optimal alignment or a nucleotide sequence as set forth in SEQ ID NO:1 or a nucleotide sequence having greater than 95% identity to SEQ ID NO:1 after optimal alignment.

Reference to greater than 92% similarity includes percentage identities and similarities greater than 92% such as 92.1%, 92.2%, 92.3%, 92.4%, 92.5%, 92.6%, 92.7%, 92.8%, 92.9%, 93%, 94%, 95%, 96%, 97%, 98%, 99% and 100%.

Reference to greater than 95% identity includes percentage identities and similarities greater than 95% such as 95.1%, 95.2%, 95.3%, 95.4%, 95.5%, 95.6%, 95.7%, 95.8%, 95.9%, 96%, 97%, 98%, 99% and 100%.

Yet another aspect of the present invention contemplates an isolated glutelin protein comprising an amino acid sequence as set forth in SEQ ID NO:2 or an amino acid sequence having greater than 96% similarity to SEQ ID NO:2 after optimal alignment.

Accordingly, the present invention also contemplates recombinant DNA constructs, as hereinbefore described, comprising the nucleic acid sequence set forth in SEQ ID NO:2 or an amino acid sequence having greater than 96% similarity to SEQ ID NO:2 after optimal alignment or a nucleotide sequence as set forth in SEQ ID NO:1 or a nucleotide sequence having greater than 96.4% identity to SEQ ID NO:1 after optimal alignment.

The constructs mentioned supra may further comprise an expression regulatory element as described herein and may also further comprise another nucleic acid sequence. For example, a construct may comprise an expression regulatory element, a nucleic acid molecule encoding a glutelin protein as herein described and may optionally comprise a further protein-encoding nucleic acid molecule, such that when expressed under the control of the expression regulatory element, the glutelin protein is fussed to the second protein.

The present invention is further described by the following non-limiting Examples:

EXAMPLE 1

Isolation of cDNA Clone

Methods
Single Pass Sequencing of cDNA Clones

A cDNA library from 12-week oil palm (*E. guieensis*) kernel tissue was constructed using oligo (dT) primer and Lambda Uni-Zap XR as the cloning vector (Stratagene). Phage plaques from the cDNA library were cored out and in vivo excised. Randomly picked cDNA clones were sequenced from the 5'-end and the results were sent for homology search to known sequence in the public database via BLASTX.

5'-RACE

First strand cDNA was synthesized from 12 waa oil palm kernel RNA using antisense sequence specific primer KRA (5' CCT GCC TTC CAG CCA ATA AG 3', SEQ ID NO:4) in a 20 µl reaction mixture containing 5 µg total RNA, 5.01 of 2 mM dNTP mix, 2.0 µl of 0.1M DTT, 1 µl of 200 U/µl Superscript reverse transcriptase (Gibco BRL) and 4 µl of 5× Superscript buffer at 42° C. for 1 hr. The RNA molecules were hydrolysed in 12.5 µl of 0.15N sodium hydroxide and 1 µl 0.5M EDTA, pH 8.0 and incubated at 68° C. for 15 min. A poly(dG) tail sequence was introduced with terminal deoxynucleotidyl transferase in a 20 µl reaction mixture containing 10 mM Tris-acetate pH 7.5, 10 mM magnesium acetate, 50 mM potassium acetate, 0.2 µl 100 mM dGTP and 0.2 µl of 300 U/µl enzyme. Second strand cDNA was synthesized in a 50 µl reaction mixture containing 5.0 µl of 2 mM dNTP, 50 pmol of anchor primer KA1 (5' CTT CCC CCC CCC CCC C 3', SEQ ID NO:5), 4.5 µl of dG-tailed single-stranded cDNA, 2.6 U of Expand High Fidelity polymerase (Boehringer Mannheim) and 5 µl of 10× enzyme buffer containing 1.5 mM $MgCl_2$. PCR conditions were as follows: 1 cycle: 95° C. for 3 min, 43° C. for 2 min. 72° C. for 2.5 min, followed b 4 cycles: 95° C. for 1 min, 43° C. for 1 min, 72° C. for 2 min. The PCR product was purified using QIAquick PCR purification kit (Qiacen), and eluted usinc 50 µl $H_2O$. A 5 µl aliquot was added to 50 µl of a secondary PCR mixture containing 5 µl of 2 mM dNTP, 50 pmol of antisense nested primer KRB (5: GAT CGC GAC CAC AGG GTT C 3' SEQ ID NO:6), 2.6 U of Expand high fidelity polymerase and 1× enzyme buffer containing 1.5 mM, $MgCl_2$. The following PCR conditions were used: 1 cycle; 95° C. for 3 min, 51° C. for 1 min. 72° C. for 30 sec, followed by 9 cycles; 95° C. for 1 min, 51° C. for 1 min, 72° C. for 1 min and 30 sec, and 80° C. soak during which 50 pmol of anchor primer KA1 was added followed by 30 cycles; 95° C. for 1 min, 51° C. for 1 min and 72° C. for 2 min. The PCR product was purified and cloned into PCRII-TOPO vector (Invitrogen).

End to End PCR

The steps involved in the production of double stranded cDNA from 12-week kernel cDNA is identical to the 5'-RACE reaction with the exception that oligo-dT primer was used to replace the sequence-specific primers KRA and KRB. The double stranded cDNA that was obtained was used as a template in PCR amplification using a pair of primers EK1 (5' AAG CAA TAG CCT TCA GCG TTT C 3', SEQ. ID NO:13) and ANEK2 (5' GCC. CTT GCT CGC AGG CCG AG 3', SEQ. ID NO: 14). The primer EK1 was designed based on the sequence information obtained from the 5'-end of the 5'-RACE product while the primer ANEK2 was obtained from the 3'-UTR region of the pOP-KT21 EST sequence.

Results

One of the 3' end ESTs of 1.1 kb from oil palm kernel cDNA library picked up the glutelin gene from oil palm and rice as the best hits from database searches using BLASTP. 5' RACE was carried out to determine the sequence at the 5'-region and to obtain the transcription start site using total RNA from kernel tissues at 12 waa. Gene-specific primer KRA and nested gene-specific primer KRB designed based on the EST sequence were used in the synthesis of first strand cDNA and the final PCR amplification step in the 5'-RACE reaction, respectively to obtain specific product of interest. The sequence information was used to produce a full-length cDNA clone by end-to end PCR using a pair of sense and antisense gene-specific primers EK1 and ANEK2 and double stranded cDNA produced from 12-week kernel tissue as template. The sequence of the full length cDNA clone designated pOP-KT21, as shown in FIG. 1, contains 1413 bp ORF (SEQ. ID NO: 1) preceeded by 45 bp of 5'-UTR and followed by 147 bp of 3'-UTR. It encodes 470 amino acid residues (SEQ. ID NO: 2) with a predicted molecular weight of 53.5 kDa.

EXAMPLE 2

Sequence Analysis

Methods

Plasmid DNA for sequencing was extracted using the Qiagen plasmid mini kit. DNA sequencing was carried out from both directions using ABI automated sequencer. The Biology Workbench Version 3.2 web-based sequence analysis tool, available at the San Diego Supercomputer Center (SDSC—UC San Diego; La Jolla, Calif.) website,t was used for sequence analysis and search for similarity between nucleotide and amino acid sequence using CLUSTALW (Thompson et al., *Nucl. Acid Res.* 22: 4673-4680, 1994).

Results

Analysis of Nucleotide Sequence

Cha and Shah (*Plant Science* 160: 913-923, 2001) have reported on the isolation of cDNA clones encoding three different isoforms of seed storage protein glutelin from oil palm, pKT7 (AF261691), pKT8 and pKT9 (AF) 93433) where pKT7 and pKT9 were full length cDNA clones. Based on sequence analysis the oil palm glutelin genes were divided into two subfamilies, subfamily A (pKT7) and subfamily B (pKT8 and pKT9). They further showed by Southern analysis that subfamily B possibly consists of at least 4 members in the oil palm genome. The nucleotide and deduced amino acid sequences of pOP-KT21 was compared with that of pKT9 and pKT7 (FIG. 2). The nucleotide sequences of pOP-KT21 and pKT9 share strong sequence identity in the coding and 3'-UTR regions with 96.4 and 90.7 sequence identities, respectively. However the sequence identity within the 5'-UTR is lower of 78.4% while the length is slightly shorter for pOP-KT21 which is 45 bp compared to pKT9, 51 bp and the sequence variation occurred does not confined to only one specific location. Several reports suggest that sequence elements within 5'-UTR regions of plant genes may play a role in regulating gene expression (Dickey et al., *Plant Cell* 3: 475-484, 1998; Bonaventure and Ohirogge, *Plant Physiology* 128: 223-235, 2002). The deduced amino acid sequence identity between pOP-KT21 and pKT9 is 96%. The region that encodes the basic subunit is more conserved with 99.5% amino acid sequence identity between pOP-KT21 and pKT9 as compared to region encoding the acidic subunit with 93.7% sequence identity. On the other hand, the nucleotide sequence homology between pOP-KT21 and pKT7 (subfamily A) is much lower with identities of only 69.8%, 48.1% and 43.6% for the coding, 3'-UTR and 5'-UTR, respectively. While the deduced amino acid sequence identity is 57.4%.

Analysis of Coding Region (Amino Acids)

Alignment of the deduced amino acid sequences of the oil palm genes (pOP-KT21, pKT7 and pKT9) with a glutelin gene from rice and a 11S globulin gene from sesame (*Sesamum indicum*) as given in FIG. 3 showed sequence homology suggesting that all these sequences are from the same evolutionary root. This is consistent with the observation for rice glutelin genes (Takaiwa et al., *Mol. Gen. Genet.* 208: 15-22, 1987) which showed sequence homology with leguminous 11S globulin genes. The position for cleavage sites for the transit leader peptide in pOP-KT21 is identical to that proposed bar Cha and Shah (supra). The transit peptide of pOP-KT21 also contains the conserved hydrophobic central core sequence FSLCLLL found in pKT7 and pKT9 suitable for mediating transfer of the protein to the lumen of the endoplasmic recticulum. It was shown that Asn and Gly-specific sequence as well as the secondary structure are important in determining the post-translational cleavage site between the acidic and basic subunits in the precursor protein (Takaiwva et al., 1987, supra). The proposed acidic region of pOP-KT21 contains 43 acidic residues (Glu and Asp) out of 285 amino acid residues. While the basic region contains 28 basic residues (Arg and Lys) out of 185 amino acid residues. The positions of the 5 cysteine residues in pOP-KT21 are consistent with that reported by Cha and Shah (supra). Four of these cysteine residues are conserved in glutelins and in all of the 11S globulins in legume and non-legume seeds (Katsube et al. in *Engineering Crop plants for Industrial End Uses*, Shewry et al. (Eds.), Portland Press, London, 1998, pp. 65-76). In pOP-KT21 these conserved cysteine residues are found at positions 24, 57 and 100 of the proposed acidic subunit and the fourth at position 7 of the proposed basic subunit The first two cysteines are involved in the formation of intrachain disulphide-bond, while the last two forms an interchain disulphide bond (Utsumi, Adv. Food Nutr. Rest. 36, 89-208, 1992; Katsube et al., supra). Formations of disulphide bond between the acidic and basic subunits stabilize the structure of seed storage proteins. Several polypeptides can be joined to form an oligomer with the proper conformation to be deposited into protein bodies (Muntz, supra).

The amino acid composition of the deduced protein sequence of pOP-KT21 is given in FIG. 4*a*. Even though the sequence of pKT7 from subfamily A is different, the amino acid profile is very similar to the glutelin protein sequences from subfamily B. It was interesting to note that oil palm kernel cake has a very similar amino acid profile (FIG. 4*b*). Notably, Arginine, Leucine, Glycine and Valine are the most predominant residues with low levels of Histidine and Tryptophan. This may suggests that glutelin is a major storage protein in oil palm kernel.

EXAMPLE 3

Northern Blot Analysis

Methods

Extraction of total RNA was performed following Siti Nor Akmar et al., (*Asia Pacific Journal of Molecular Biology and Biotechnology* 2(2): 113-118, 1994). Slot blot and Northern blot analyses were carried out as described by Siti Nor Akmar (PhD Thesis, University of East Anglia, 1999). The analysis were performed using the pOP-KT21 EST as probe using high stringency washing condition. Northern blot analysis was also carried out using gene-specific probe designed based on the sequence from the 5'-UTR region of pOP-KT21. The two primers used to produce the gene-specific probe from the 5'-UTR and 14 bases at the 5'-end of the coding region of pOPKT21 were KTC (5' CAA TAG CCT TCA GCG TTT C 3'. SEQ ID NO:7) and KTD (5'GAG AAG GAC GAC ATG GCT.3', SEQ ID NO:8)

Results

Figure 6:
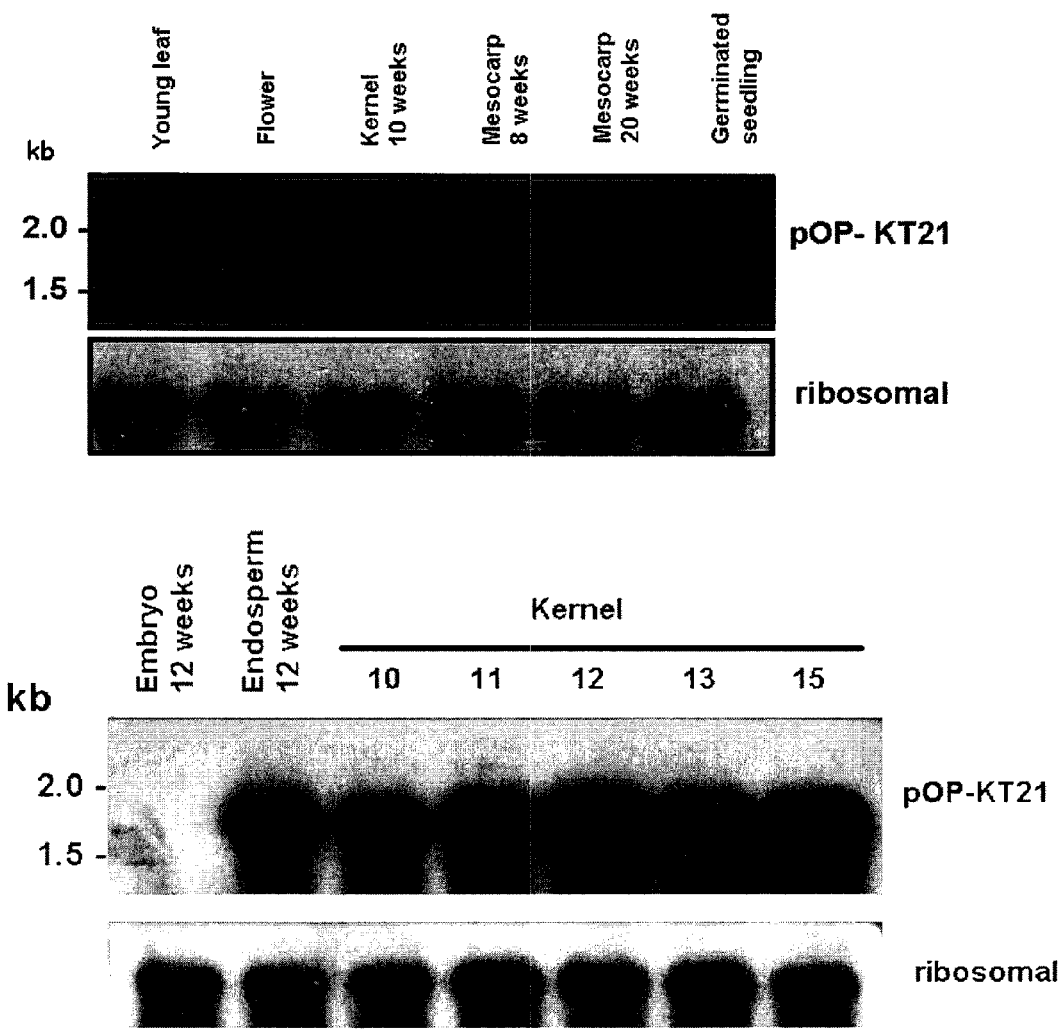
FIG. 6 is a graphical representation showing the expression pattern of glutelin genes (subfamily B) in different oil palm tissues. Northern blot containing 20 μg total RNA from various oil palm (*E. guineensis*) tissues as indicated was hybridised with $^{32}$P-labelled probe containing pOP-KT21 cDNA sequence. The membrane was reprobed with ribosomal DNA to check for equal loading of % NA samples.

Slot blot analysis was carried out using the pOP-KT21 EST as probe and total RNA from various oil palm tissues (FIG. 5). High level of expression was observed in kernel tissues. It also demonstrates that the expression of oil palm glutelin is tightly regulated where expression is also not detectable in germinated seedlings and flowers at fronds 10, 14 and 19. The results of the northern blot analysis using pOP-KT21 as probe (FIG. 6) confirmed that the transcript size is about 1.6 k-b. It further confirms that this gene is highly expressed only in the kernel, with no detectable expression in young leaf, flower, germinated seedlings and mesocarp of immature (8 waa) and ripe fruits (20 waa). It is highly expressed throughout the different stages of kernel development (10-15 waa), with higher expression levels after 12 waa (FIG. 6). The results obtained from the slot blot and northern blot analysis using pOP-KT21 as probe confirmed the expression profile for the subfamily B as demonstrated by Cha and Shah (*Plant Science* 160: 913-923, 2001). The pOP-KT21 probe was further used to determine the specific site of expression in the kernel (FIG. 6). It was demonstrated for the first time that in the kernel, the expression is confined to the endosperm and no expression was detected in the embryo. Since the endosperm is the site of oil synthesis in oil palm kernel, the promoter of pOP-KT21 may be used to regulate expression of transgenes to modify kernel oil composition without interfering with mesocarp oil synthesis.

Figure 7:
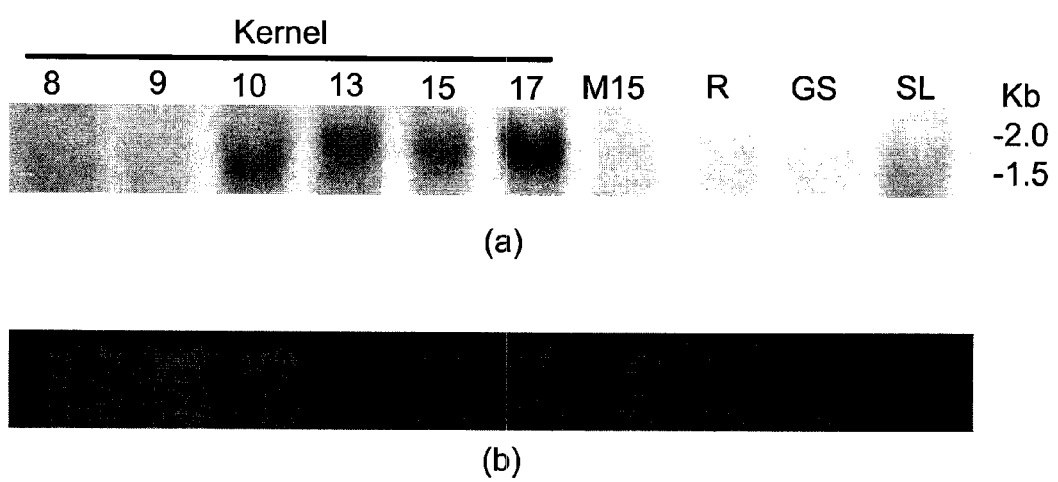
FIG. 7 is a graphical representation showing the expression pattern of pOP-KT21 in different oil palm tissues. Northern blot (7a) containing 20 μg total RNA from various oil palm (*E. guineensis*) tissues was hybridised with $^{32}$P-labelled gene-specific probe prepared from 5'-UTR and 14 bases from the 5'-end of the coding region of pOP-KT21. The RNA samples were from kernel at 8, 9, 10, 13, 15 and 17 weeks after anthesis, mesocarp at 15 weeks after anthesis (M15), roots (R), germinated seedlings (GS) and spear leaves (SL). An ethidium bromide stained gel (7b) was included to show equal loading of RNA samples.

Since the sequence at the 5'-UTR region of pOP-KT21 and pKT9 shows higher variability than the 3'-UTR, region, a gene-specific probe was prepared based on pOP-KT21 5'-UTR sequence and 14 bp 5'-end coding sequence which also show high level of variability and used in northern blot analysis (FIG. 7) with high stringency washing condition. It was demonstrated that pOP-KT21 contributed to the high level of expression in the kernel and its expression profile correlated well with the expression profile of the glutelin genes belonging to subfamily B. This confirms that the expression of pOP-KT21 is regulated by a kernel-specific promoter.

EXAMPLE 4

In-situ Hybridization

Methods

Probe Synthesis

The oil palm 1.1 kb EST containing partial a sequence of pOP-KT21 was cloned into TOPO-TA plasmid (Invitrogen). A reaction mixture containing 1 µg plasmid clone, 2 µl 10×DIG PNA labelling mix (Roche), 2 µl 10× Transcription Buffer (400 mM Tris-HCl pH 8.0, 100 mM $MgCl_2$, 100 mM Dithiothreitol and 20 mM spermidine), 2 µl RNA polymerase (SP6 or T7) and sterile $H_2O$ to a final volume of 20 µl was prepared and incubated for 2 hours at 37° C. The reaction was stopped by adding 0.8 µl of 0.2 M EDTA (pH 8.0). The labelled RNA transcript was purified using QIAquick PCR Purification Kit (Qiagen). The probe was diluted to 0.2-10 ng/µl in the hybridization buffer.

In situ Section Pre-treatment

Fixation, embedding and sectioning of tissue were performed based on the methods of Weigel and Glazebrook (*ARABIDOPSIS: A Laboratory Manual*, Cold Spring Harbor Laboratory Press, Cold Spring Harbor, N.Y., 2002). The tissue sections were deparaffinized 2× in Histoclear for 10 min.

The section was hydrated through ethanol series: 2×100% ethanol for 1-2 min. 95% ethanol for 1-2 min. 90% ethanol for 1-2 min, 80% ethanol for 1-2 min, 60% ethanol for 1-2 min, 30% ethanol for 1-2 min, and finally 1120 for 1-2 min. The slides were then immersed in 2×SSC at room temperature for 15-20 min then transferred to proteinase K (1 µg/ml) solution in 100 mM Tris-HCl pH 8.0, 50 mM EDTA at 37° C. for 30 min. Proteinase K was blocked with 2 mg/ml glycine in PBS room temperature for 2 min followed by washing 2× in PBS room temperature for 2 min. The tissue was fixed in 4% paraformaldehyde pH 7 at room temperature for 10 min followed by washing 2× in PBS at room temperature for 5 min. The slides were transferred to 0.5% (v/v) acetic anhydride in 0.1M triethanolamine pH 8. This was followed by washing 2× in PBS at room temperature for 5 min. The slides were dehydrated by moving them through the following solutions: 30% ethanol for 30 sec. 60% ethanol for 30 min. 80% ethanol for 30 sec, 90% ethanol for 30 sec. 95% ethanol for 30 sec and 2×100% ethnol for 30 sec. The slides were stored in a container a small amount of ethanol for several hours at 4° C.

In situ Hybridization

Hybridization solution (enough for 5 slide pairs) was prepared as follows: 100 µl 10× in situ salts, 400 µl deionized formamide, 200 µl 50% dextran sulfate, 20 µl 50×denhardts solution, 10 µl tRNA (100 mg/ml), 70 µl H$_2$O, which made up to the total volume of 800 µl. For each pair of slides, probe was added to 40 µl of 50% formamide, heated to 80° C. for 2 min, spun down and kept on ice. Hybridization solution (160 µl) was added to each pair of slides. The probe was applied by spreading 100 µl to each slide with the side of the pipette tip so that all the tissue was exposed to the probe without generating bubbles. The slides were sandwiched slowly. The slides were covered with Parafilm and hybridisation was performed at 50°-55° C. overnight.

Washing and Signal Detection

The slides were rinsed in 0.2×SSC at 55° C. to separate them. The wash in 0.2×SSC was repeated for another 60 min with gentle agitation. This was followed by washing 2× in NTE (10 mM Tris pH 8.0, 0.5 M NaCl, 5 mM EDTA) at 37° C. for 5 min and 1× in NTE containing RNAse (20 µg/ml) at 37° C. for 5 min. After rinsing with NTE the slides were placed in 0.2×SSC at 55° C. with gentle for 60 mins followed by 1×PBS at room temperature for 5 min. The slides were incubated in Boehringer blocking solution in 100 mM Tris-HCl pH 7.5 and 150 mM NaCl for 45 min. The block was replaced with 1.0% BSA in 100 mm Tris-HCl pH7.5, 150 mM NaCl, 0.3% Triton X-100 for 45 minutes. Anti-DIG antibody was diluted (1:1250) in buffer A (0.1M tris pH 7.5, 0.15 M NaCl, 1% (w/v) BSA and 0.3% (v/v) Triton X-100) and puddle in a plastic dish. The slides were sandwiched together and the solution was pulled up by capillary action and incubation was performed for 2 h at room temperature. The slides were then washed 4× in buffer A for 20 min each wash, with gentle agitation followed by washing in detection buffer 2×. Fresh NBT/BClP mix was applied and the slides were sandwiched to draw up the solution by capillary action. The slides were placed in a humidified chamber in total darkness for 1-3 days. The slides %% ere rinsed in TE to stop the reaction. The slides were then viewed under the light microscope.

Results

In situ hybridisation was carried out on oil palm kernel tissue sections using sense and antisense RNA probes generated from the oil palm 1.1 kb EST sequence of pOPKT21. Hybridising signals obtained using the antisense probe showed a uniform distribution of transcripts in the endosperm where hybridising signals were observed in all of the parenchyma cells of the endosperm (FIG. 8). The endosperm is composed of a homogenous cell type, namely the parenchyma cells. These cells play important roles in the storage of proteins and oils. Observation of endosperm section from mature coconuts under 6× magnification, for example, showed that the parenchyma cells were occupied with large globules of oil and small granules of protein (Brown, *The Plant Kingdom*, Blaidsdell Publishing. Company, New York, 1935). Thus seed storage protein gene promoters can direct accurate spatial regulation of genes involved in both protein and oil synthesis because both storage products are produce in the same type of cells.

EXAMPLE 5

Promoter Isolation

Methods

Isolation of the mesocarp-specific promoter was carried out using the Universal Genome Walker Kit (Clontech). Total DNA was isolated and purified from oil palm spear leaves using DNeasy Plant Mini Kit (Qiagen). Aliquots containing 2.5 µg DNA were digested with restriction enzymes Dra I, Eco RV, Pvu U and Stu I that produce blunt ends and ligated to the GenomeWalker Adaptor creating the GenomeWalker libraries. Primary PCR was performed using 12 µl aliquots of each library with antisense gene-specific primer GK4 (5' GAC TGG ACC CAA ATT GAG CCT GGG ACA C 3'. SEQ ID NO:9) from 5 terminal of the coding region of pOP-KT21 and primer API provided with the Kit. The PCR product was diluted 50× and 1 µl vas used in secondary PCR reaction using antisense nested gene-specific primer GKN6 (5 GAA AGA GAG AAA CGC TGA AGG CTA TTG C 3'. SEQ ID NO:10) from the 5-end within the 5'-UTR of the cDNA and primer AP2 from the Kit. PCR was carried out using Advantage Tth Polymerase Mix from Clontech and Perkin-Elmer 9600 thermal cycler following cycle conditions recommended in the GenomeWalker Kit Manual. The primary and secondary PCR products were analysed and purified from agarose gel using gel extraction kit from Qiagen and cloned into the PCRII-TOPO vector (Invitrogen). The recombinant clone was sequenced using M13 forward and reverse primers.

Results

Figure 9:
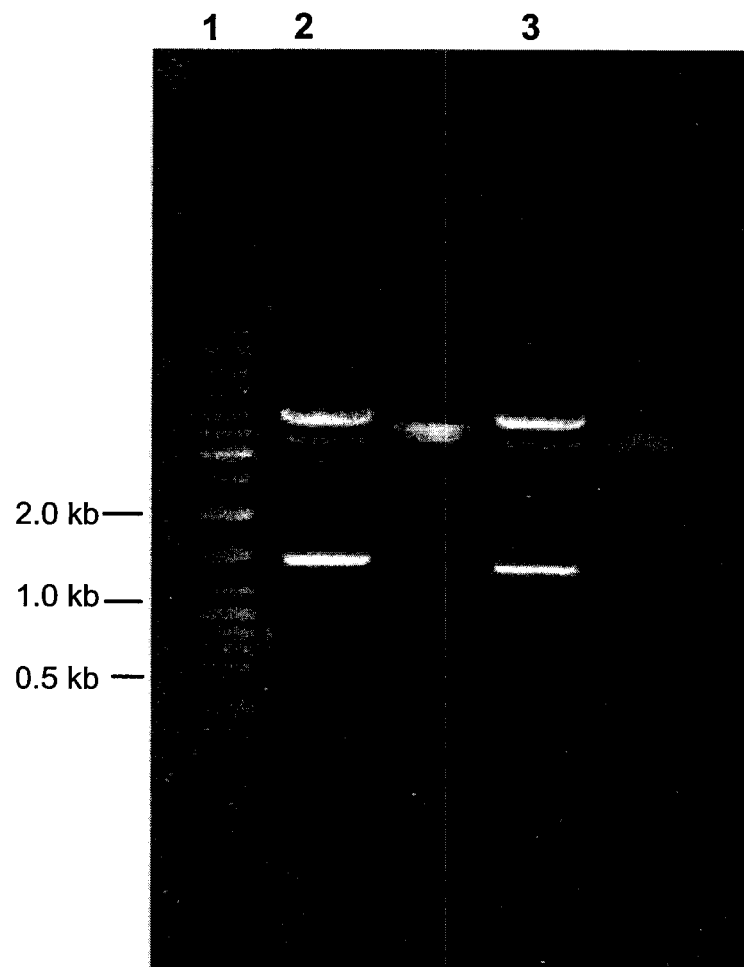
FIG. 9 is a photographic representation of an agarose gel showing the products of genome walking used to isolate the pOP-KT21 gene promoter. The primary PCR reaction was performed using the gene-specific primer, GK4, from the 5'-sequence of the pOP-KT21 coding region, primer API and oil palm Eco RV genome walker library as template, the primary PCR product was used in a secondary PCR reaction using primers AP2 and the nested gene-specific primer, GKN6 from the 5'-UTR of pOP-KT21. The amplified NA fragments from both reactions were subsequently purified from the agarose gel and cloned into the PCR II TOPO vector for sequencing. Lane 1 is the molecular weight marker, Lane 2 shorts the genome walker primary PCR product and Lane 3 is the secondary PCR product.

The Universal GenomeWalker kit from Clontech was used to clone the promoter or the 5' upstream regulatory region of pOP-KT21. Aliquots from Dra I, Eco RV and Stu I oil palm GenomeWalker libraries were amplified using a 28-mer gene-specific primer (GK4) from 5'-terminal of pOP-KT21 coding region for the mature protein and primer AP1 (adaptor sequence) provided with the kit. The region where GK4 is obtained showed a relatively higher sequence variability between pOP-KT21 and pKT9 compared to the rest of the coding region. The nucleotide sequence identity between pOP-KT21 and pKT9 in this region is only 82%. The Dra I: Eco RV and Stu I libraries produced PCR products of about 1.2 kb, 1.5 kb and 0.45 kb, respectively. Since the product of the Eco RV library was the biggest, it was selected for further PCR reaction. One microliter of 1/50 dilution of the primary PCR product was used in a second round PCR reaction. In this reaction a 28-mer nested gene-specific primer (GKN6) and nested primer from the Adaptor sequence (AP2) were used. This secondary PCR reaction specifically amplified fragments containing the pOP-KT21 sequence. Fragments produced in the primary PCR reaction due to non-specific binding of primers would not be amplified. FIG. 9 shows the product of the primary and secondary PCR reactions. The size of the band obtained from the secondary PCR reaction was about 1.4 kb. This is the expected size using the pair of nested primers because the sequence of GKN6 is only about 100 bp internal to GK4. The bands from both primary and secondary PCR reactions were purified from the agarose gel and cloned into PCR 11 TOPO vector (Invitrogen). Apart from being about 100 bp shorter at the 3-end, the sequences of all the 5 clones from the secondary PCR reaction were identical to that of the primary PCR product A genomic clone from the primary PCR product was used in subsequent analysis. The clone consists of 1479 bp genomic fragment containing 1347 promoter region, SEQ ID NO: 3 (FIG. 10). The nucleotide sequence of the overlapping region of this genomic fragment with the 5'-terminal sequence of pOP-KT21 cDNA is totally homologous (FIG. 11), indicating that it is actually the promoter for pOP-KT21 and not of pKT9 which has 15 different nucleotides in this region. The transcription start site and TATA box were identified in the promoter region as well as AACA and Skn-1-like motifs which are of importance in regulating endosperm-specific expression of rice glutelin gene, GluB-J (FIG. 10).

EXAMPLE 6

Cloning of the pOP-KT21 Promoter Into pEGFP-1

Methods

Two primers were used for cloning a 1375 bp genomic fragment containing the 1347 bp promoter sequence into the multiple cloning site of pEGFP-1 (Clontech), a promoterless vector with GFP as reporter gene to produce GluP-EGFP. The first primer GAK5 (5' CCG CTC GAG TCA AAT TAT CAA AAT ATC 3', SEQ ID NO:11) is a sense primer from 5' end of the promoter with an Xho I site introduced. The second primer GAK4 (5' CGC GGA TCC AAG AGA GAA ACG CTG 3', SEQ ID NO:12) is an antisense primer 17 bases upstream of the translation start site with a Bam HI site introduced.

The PCR reaction mixture (50 µl) for amplifying pOP-KT21 promoter contained 5.0 µl of 2 mM dNTP, 3.3 µl of 15M GAK5 primer, 3.3 µl of 15 µM GAK4 primer, 25 ng of plasmid pKT21-Pa, 5.0 µl of 10× enzyme buffer containing 1.5 mM MgCl$_2$ and 2.6 U Expand High Fidelity Polymerase (Roche). PCR conditions were as follows: 1 cycle; 94° C. for 3 min, 20 cycles; 94° C. for 1 min, 58° C. for 1 min and 72° C. for 90 sec followed by I cycle; 72° C. for 10 min. The PCR product was purified using QIAquick PCR purification kit (Qiagen). Ligation was performed using 1:3 molar ratio of vector; insert in 15.0 pd reaction volume containing 1.5 µl 10× ligase buffer and 1.5 µl of T4 DNA ligase (1 U/µl) and incubation at 16° C. O/N. Two microliters were used to transform competent cells JM101 as described in Siti Nor Akmar (1999, supra). The cells were spread on LB plate containing 50 µg/µl ampicillin to select for transformed cells. Plasmid DNA was prepared from the bacterial colonies using QIAprep spin miniprep kit (Qiagen). Restriction analysis was carried out by digesting with Xho I and Bam HI to confirm the size of insert. Sequencing of GluP-EGFP was carried out using EGFP-N sequencing primer (Clontech).

Results

Figure 12:
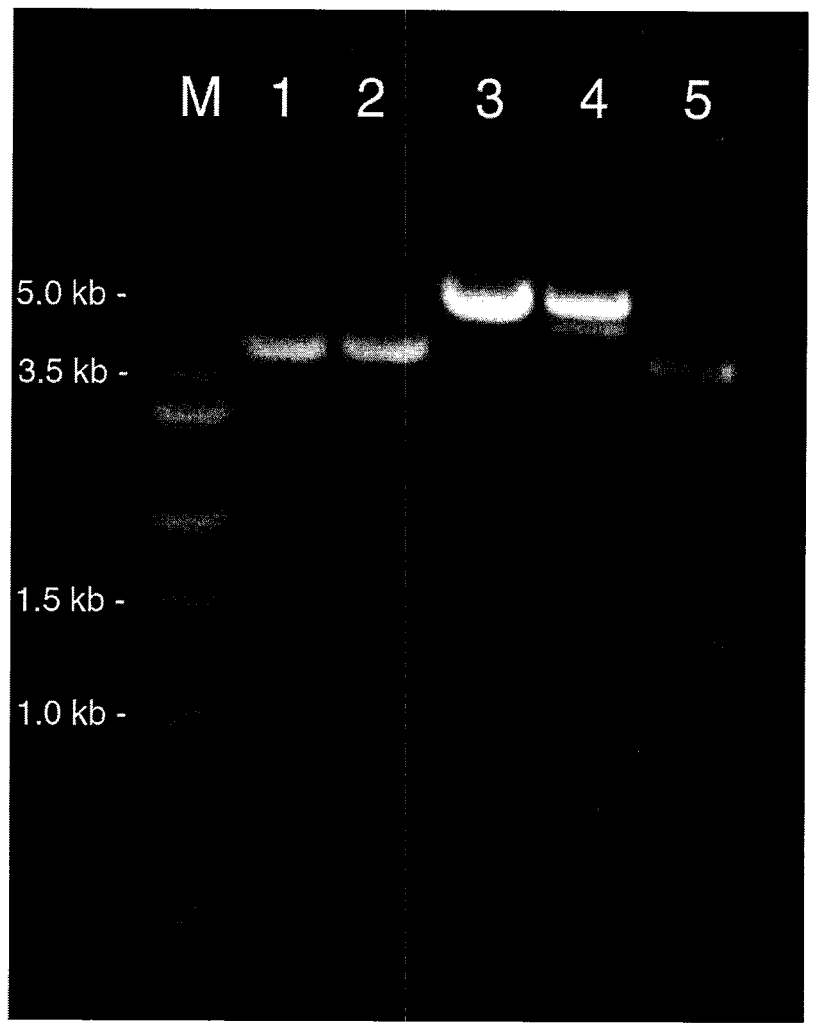
FIG. 12 is a photographic representation of an agarose gel showing the results of restriction analysis of the chimeric transformation vector GluP-EGFP. GluP-EGFP was produced by introducing the oil palm glutelin gene (pOP-KT21) promoter into the Bam HI and Xho I sites found in the multicloning region of the pEGFP-1 vector (Clontech), which contains GFP as the reporter gene. Lanes 1 and 3: pEGFP-1 and GluP-EGFP digested with Bam HI, respectively. Lanes 2 and 4: pEGFP-1 and GluP-EGFP digested with Xho I, respectively. Lane 5: GluP-EGFP digested with Bam I and Xho I. Lane M: DNA ladder marker (Fermentas)

The 1375 bp genomic fragment containing the 1347 bp promoter region was cloned into a promoterless transformation vector pEGFP (Clontech) containing GFP as reporter gene and the chimeric transformation vector produced was designated GluP-EGFP. In EGFP the cryptic intron, which has resulted in non-functional protein in *Arabidopsis* (Haseloff and Amos, *Trends Genet.* 11: 328-329, 1995) has been removed. An amino acid mutation (Phe-64 to Leu) was also introduced for enhancing the fluorescent signals. Restriction analysis of GluP-EGFP with Xho I and Bam HI showed successful cloning of the 1375 bp genomic fragment in pEGFP (FIG. 12) and is supported by sequence data obtained using EGFP-N primer (Clontech).

EXAMPLE 7

Biolistic Method and Transient Expression for Promoter Analysis

Methods

Preparation of Tissue Slices, Bombardment Parameters and Detection of GFP Spots in Bombarded Tissues Oil palm mesocarp and endosperm of fruits at 12 w.a.a and spear leaves were sterilized by soaking in RBS for 15 minutes followed by 25% chlorox for 15 min for mesocarp and endosperm and 10% chlorox for leaves. The tissues were then rinsed several times with sterile distilled water before culturing.

For one liter of culture media, 4.41 g MS salts and 30 g sucrose were used. The media were adjusted to pH 5.8 with 1M NaOH and solidified with 0.8% (w/v) phyto agar. The oil palm mesocarp, endosperm and leaves were cut into small slices of approximately 1 cm×1cm in diameter. The explants were placed on the culture media and kept at 28° C. in the dark for 24-48 hours before bombardment. The oil palm tissue slices were bombarded it with the Biolistic™ particle delivery system, PDS-1000/He (Biorad U.S.A). The chamber and macrocarrier were sterilized with 100% ethanol before use.

Sixty micrograms of the microcarrier (1.0 µm in size gold particle) were placed in 1 ml of 100% ethanol in microcentrifuge tube followed by vortexing then centrifuging for 1-2 minutes at 12,000 rpm and the supernatant was subsequently removed. This procedure was repeated 3 times. One microliter of sterile H$_2$O was added, the mixture was sonicated for 5 sec before centrifugation and subsequent removal of the supernatant. This step was repeated 3 times. The gold particles were finally resuspended in 1 ml of sterile distilled water and aliquoted into 50 µl volume.

Plasmids were isolated using a Qiagen Spin Miniprep Kit. Ten micrograms of DNA was added to the 50 µl aliquot of gold. For experiments with an internal control, 5 µg pBI221 plasmid containing CaMV promoter with GUS as a reporter gene was added to 10 µg of the promoter construct having GFP as the reporter gene prior to mixing with the 50 µl aliquot of old particles. One hundred microliters of 2.5M CaCl$_2$, 40 µl 0.1M spermidine was then added while vortexing. The mixture was centrifuged at 10,000 rpm. The supernatant, was removed and the microcarrier was washed with 100% ethanol. These steps were repeated twice and finally, the microcarrier was resuspended in 60 µl ethanol and kept at −20° C. until used.

For each bombardment, 8 gi of DNA-coated gold particles were loaded on a macrocarrier and allowed to dry. The mesocarp and endosperm tissues were bombarded with 1550 Psi helium pressure and 9 cm distance between macrocarrier and target tissue. The leaves (control tissues) were bombarded at 1100 with 6 cm distance between macrocarrier and target tissue. The vacuum pressure was maintained at 27" Hg.

GFP expression was determined by counting the green fluorescence spots produced visualised under a Leica fluorescence microscope fitted with a GFP filter set.

GUS Histochemical Assay

Enzymatic GUS assay was carried out using X-Gluc (5-bromo-4-chloro-3-indolyl-β-D-glucuronide) as a substrate, following the procedure described by Jefferson et al., (1987) with some modifications. After analysis for the presence of GFP fluorescent spots, the transformed endosperm, mesocarp, land leaf tissue slices from each co-bombardment were placed separately in sufficient amount of GUS staining solution (0.1M NaPO$_4$ buffer, pH 7.0, 10 mM EDTA, pH 7.0, 0.5 mM K Ferricyanide, pH 7.0, 0.5 mM K Ferrocyanide, pH 7.0, 10 mM X-Gluc, and 0.1% Triton-X) without performing any pre-fixation procedure. The tissue container was covered in order to prevent the evaporation of the reagent mixture and then incubated at 37° C. for 12 h. The enzymatic activity utilizes X-Gluc as substrate to produce blue precipitates which were observed as blue spots in different tissues under the white spectrum using Nikon SMZ1000 microscope Results Bombardment parameters that have been optimized for promoter analysis in oil palm mesocarp and leaf tissues by transient assay (Zubaidah and Siti Nor Akmar, *Journal of Oil Palm Research* Vol. 15 No. 2: 62-69, 2003) were used in analyzing the oil palm pOP-KT21 promoter. In addition, various conditions for performing promoter analysis by transient assay of reporter gene in oil palm kernel tissue slices was investigated using constitutive CaMV promoter—green fluorescent protein (GFP) reporter gene construct. It was found that the number of fluorescent spots increased by more than 20 folds when the tissue slices used for bombardment were obtained from the outer layer of the endosperm. This was achieved using helium pressure of 1550 Psi and distance between macrocarrier and target tissue of 9 cm (FIG. 13). This condition was subsequently used in analyzing pOP-KT21 promoter activity.

The pOP-KT21 promoter was cloned into a promoterless transformation vector pEGFP (Clontech) which contains the green fluorescent protein (GFP) as a reporter gene, producing a vector construct designated GluP-EGFP. This gene construct was bombarded into oil palm kernel, mesocarp and leaf tissue slices. Comparison of GFP expression was made with tissue slices bombarded with GFP gene construct containing CaMV promoter (CaMV-EGFP) and as negative control, tissues bombarded with promoterless vector construct (pEGFP) were also analysed.

Figure 14:
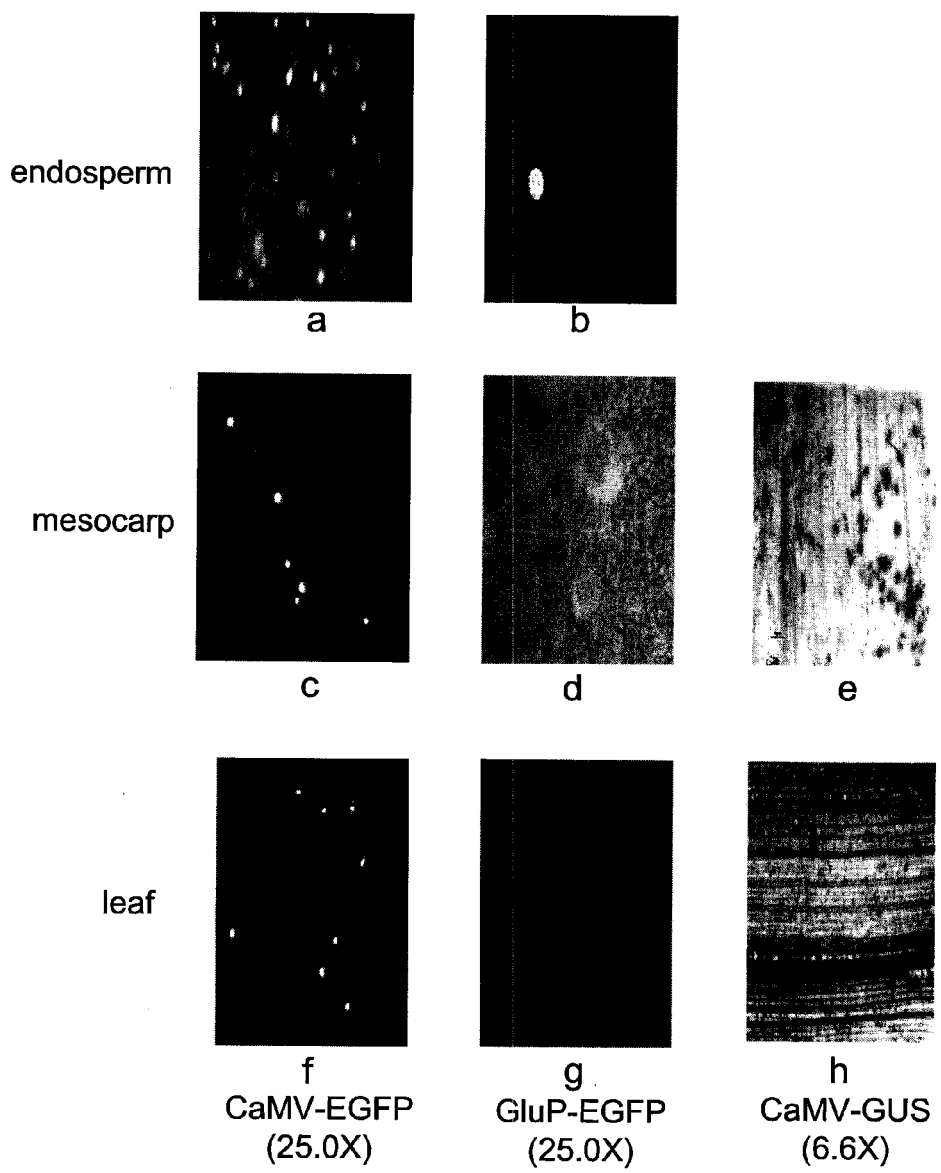
FIG. 14 are photographic representations of endosperm, mesocarp and leaf tissues bombarded with GluP-EGFP and CaMV-EGFP (positive control). Promoter-reporter gene assay was performed to confirm endosperm-specific activity of the oil palm glutelin gene promoter (GluP) by comparing expression of green fluorescent protein in oil palm endosperm, mesocarp and leaf tissues bombarded with GluP-EGFP (b, d and g, respectively) and CaMV-EGFP (a, c and f, respectively). As internal control tissues d and g were also co-bombarded with CaMV-GUS and expression of GUS were detected in these tissues as shown in e and h respectively.

Transient expression of GFP observed as green fluorescence spots was detected in the kernel tissue slices bombarded with GluP-EGFP but expression of GFP was not detected in mesocarp and leaf tissues bombarded with this gene construct (FIGS. 14 and 15) even though expression of co-bombarded uidA (GUS) occurred under the regulation of CaMV promoter (FIG. 14). Green fluorescent spots could be detected in kernel, mesocarp and leaf tissue slices bombarded with CaMV-EGFP (FIGS. 14 and 15). Fluorescent spots were not found in any of the tissue slices bombarded with the promoterless vector, pEGFP (FIG. 15). Based on the comparison of the activity of the CaMV and oil palm glutelin gene (pOP-KT21) promoter as indicated by the transient expression of GFP, it can be concluded that the oil palm pOP-KT21 promoter is a functional promoter with kernel-specific promoter activity.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

BIBLIOGRAPHY

Altschul et al., *Nucl Acids Res.* 25:3389-3402, 1997
Ausubel et al., *Current Protocols in Molecular Biology*, John Wiley & Sons Inc, 1994-1998, Chapter 15, 1998;
Beyer et al., *Proceedings of the American Society for Nutritional Sciences Symposium on Plant Breeding:* 506S-510S, 2002;
Bonaventure and Ohlrogge, *Plant Physiol.* 128: 223-235, 200';
Brown, *The Plant Kingdom*, Blaidsdell Publishing Company, New York, 1935;
Cha and Shah. *Plant Science* 160: 91.3-923, 2001;
Daniell et al., *Trends in Plant Science* 6(5): 219-226, 2001;
Dickey et al, *Plant Cell* 3: 475-484, 1998;
Galas and Schmitz, *Nucl. Acids Res.* 5: 3157-3170, 1978;
Haseloff and Amos, *Trends Genet.* 11: 328-329, 1995;
Katsube et al., in *Engineering Crop plants for Industrial End Uses*, Shewry et al. (Eds.), Portland Press, London, 1998, pp. 65-76;
Kinney, *Journal of Food Lipids* 3, 273-292, 1996;
Muntz, *Plant Molecular Biology* 38: 77-99, 1998;
Sanford and Wolf, U.S. Pat. No. 4,945,050;
Schmitz, *Nucl. Acids Res.* 5: 3157-3170, 1978;
Shewry, *Biol. Rev.* 70: 375-426, 1995;
Siew, *PORIM Buletin* 19: 19-22, 1989;
Siti Nor Akmar et al. *Asia Pacific Journal of Molecular Biology and Biotechnology* 2(2): 113-118, 1994;
Siti Nor Akmar, PhD Thesis, University of East Anglia, 1999;
Stomp et al. U.S. Pat. No. 5,122,466;
Tackaberrry et al., *Genome* 46(3): 521-526, 2003;
Takaiwa et al., *Mol. Gen. Genet.* 208:15-22, 1987;
Takaiwa et al., *Plant Mol. Biol.* 17(4): 875-885, 1991;
Thompson et al., *Nucl. Acid Res.* 22: 4673-4680, 1994;
Utsumi, *Adv. Food Nutr.* Res. 36.89-208, 1992;
Voelker et al. *Science* 257: 72-73, 1992;
Weigel and Glazebrook, *ARABIDOPSIS: A Laboratory Manual*, Cold Spring Harbor Laboratory Press, Cold Spring Harbor, N.Y. 2002;
Zubaidah and Siti Nor Akmar, *Journal of Oil Palm Research* Vol. 15 No. 2: 62-69, 2003.

The invention claimed is:

1. An isolated nucleic acid molecule comprising a promoter comprising the nucleic acid sequence as set forth in SEQ ID NO:3 or functional fragments of SEQ ID NO:3 which drive gene expression in the endosperm of a plant, wherein the promoter operably linked to a heterologous sequence.

2. The isolated nucleic acid molecule of claim 1 further comprising an expression regulatory element, where the expression regulatory element comprises an enhancer and/or silencer.

3. The isolated nucleic molecule acid of claim 1, wherein said promoter is from a plant glutelin gene.

4. The isolated nucleic molecule acid of claim 3, wherein said plant is an oil palm.

5. The isolated nucleic molecule acid of claim 4, wherein said plant is of the genus *Elaeis*.

6. The isolated nucleic molecule acid of claim 5, wherein said plant is of the species *Elaeis guineensis* or *Elaeis oleifera*.

* * * * *